US006400352B1

(12) United States Patent
Bruneau et al.

(10) Patent No.: US 6,400,352 B1
(45) Date of Patent: *Jun. 4, 2002

(54) MECHANICAL AND FORCE TRANSMISSION FOR FORCE FEEDBACK DEVICES

(75) Inventors: Ryan D. Bruneau, Sunnyvale; Kenneth M. Martin, Palo Alto; Louis B. Rosenberg, San Jose; David F. Moore, Redwood City; Bruce M. Schena, Menlo Park, all of CA (US)

(73) Assignee: Immersion Corporation, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/138,304

(22) Filed: Aug. 21, 1998

Related U.S. Application Data

(63) Continuation-in-part of application No. 08/870,956, filed on Jun. 6, 1997, now Pat. No. 6,246,390, which is a continuation of application No. 08/374,288, filed on Jan. 18, 1995, now Pat. No. 5,731,804.

(51) Int. Cl.[7] ................................................ G09G 5/00
(52) U.S. Cl. ....................................... 345/156; 345/161
(58) Field of Search ................................ 345/156, 157, 345/161, 162, 179; 74/471; 33/1 M, 1 N, 1 MP, 1 PT, 504, 505; 200/6 A; 338/128; 414/5; 901/46, 16; 434/45

(56) References Cited

U.S. PATENT DOCUMENTS

| | | | |
|---|---|---|---|
| 2,906,179 A | 9/1959 | Bower | 90/13.5 |
| 3,490,059 A | 1/1970 | Paulsen et al. | 73/133 |
| 3,795,150 A | 3/1974 | Eckhardt | 74/5.4 |

(List continued on next page.)

FOREIGN PATENT DOCUMENTS

| | | |
|---|---|---|
| JP | 4-34610 | 5/1990 |
| WO | WO9426167 | 11/1994 |
| WO | WO9510080 | 4/1995 |
| WO | WO9520788 | 8/1995 |
| WO | WO9532459 | 11/1995 |

OTHER PUBLICATIONS

Adelstein B. et al., "Design and Implementation of a Force Reflecting Manipulandum for Manual Control Research," 1992, pp. 1–24.

Buttolo, P. et al., "Pen–Based Force Display for Precision Manipulation in Virtual Environments," IEEE 0–8186–7084, 1995, pp. 217–224.

(List continued on next page.)

*Primary Examiner*—Chanh Nguyen
(74) *Attorney, Agent, or Firm*—James R. Riegel; Paul Thyfeut

(57) ABSTRACT

A force feedback interface device includes improvements in a mechanical linkage and drive mechanism. The force feedback device is coupled to a host computer and includes a user manipulatable object graspable by a user, at least one actuator that outputs a force on the user object, and a sensor for sensing motion of the user object. A linkage mechanism provides the user object with degrees of freedom and includes five members rotatably coupled to each other. The linkage mechanism supports the bearings of the device with protrusions rotatably coupled to central members of the linkage. The drive mechanism is preferably a belt drive that includes an idler positioned adjacent to a drive pulley and which impedes radial displacement of a belt away from the drive pulley, and thus impedes losing positive engagement of the belt, without preloading the belt. The idler can be a passive idler that does not contact the belt during operation and/or an active idler that continuously contacts the belt. Some or all portions of the linkage mechanism and the drive mechanism are preferably symmetrical, allowing low cost manufacture of the device.

35 Claims, 10 Drawing Sheets

U.S. PATENT DOCUMENTS

| | | | |
|---|---|---|---|
| 3,875,488 A | 4/1975 | Crocker et al. | 318/648 |
| 3,919,691 A | 11/1975 | Noll | 340/172.5 |
| 3,944,798 A | 3/1976 | Eaton | 235/151.3 |
| 4,148,014 A | 4/1979 | Burson | 340/709 |
| 4,216,467 A | 8/1980 | Colston | 340/356 |
| 4,436,188 A | 3/1984 | Jones | 188/378 |
| 4,448,083 A | 5/1984 | Hayashi | 73/862.04 |
| 4,477,043 A | 10/1984 | Repperger | 244/223 |
| 4,604,016 A | 8/1986 | Joyce | 414/7 |
| 4,676,002 A | 6/1987 | Slocum | 33/1 MP |
| 4,775,289 A | 10/1988 | Kazerooni | 414/735 |
| 4,782,327 A | 11/1988 | Kley et al. | 340/365 P |
| 4,800,721 A | 1/1989 | Cemenska et al. | 60/393 |
| 4,803,413 A | 2/1989 | Kendig et al. | 318/648 |
| 4,811,608 A | 3/1989 | Hilton | 73/862.04 |
| 4,861,269 A | 8/1989 | Meenen, Jr. | 434/45 |
| 4,879,556 A | 11/1989 | Duimel | 341/20 |
| 4,949,119 A | 8/1990 | Moncrief et al. | 364/578 |
| 4,961,267 A | 10/1990 | Herzog | 33/503 |
| 4,962,448 A | 10/1990 | DeMaio et al. | 364/146 |
| 4,982,618 A | 1/1991 | Culver | 74/471 XY |
| 5,007,300 A | 4/1991 | Siva | 74/471 |
| 5,044,956 A | 9/1991 | Behensky et al. | 434/45 |
| 5,103,404 A | 4/1992 | McIntosh | 318/568.22 |
| 5,107,080 A | 4/1992 | Rosen | 200/6 A |
| 5,116,180 A | 5/1992 | Fung et al. | 414/5 |
| 5,142,931 A | 9/1992 | Menahem | 74/471 |
| 5,143,505 A | 9/1992 | Burdea et al. | 414/5 |
| 5,156,363 A | 10/1992 | Cizewski et al. | 244/223 |
| 5,184,319 A | 2/1993 | Kramer | 364/806 |
| 5,185,561 A | 2/1993 | Good et al. | 318/432 |
| 5,193,963 A | 3/1993 | McAffee et al. | 414/5 |
| 5,197,003 A | 3/1993 | Moncrief et al. | 364/410 |
| 5,223,776 A | 6/1993 | Radke et al. | 318/568.1 |
| 5,228,356 A | 7/1993 | Chuang | 74/471 XY |
| 5,251,127 A | 10/1993 | Raab | 364/413.13 |
| 5,264,768 A | 11/1993 | Gregory et al. | 318/561 |
| 5,296,846 A | 3/1994 | Ledley | 345/161 |
| 5,297,057 A | 3/1994 | Kramer et al. | 364/512 |
| 5,327,790 A | 7/1994 | Levin et al. | 73/862.325 |
| 5,379,663 A | 1/1995 | Hara | 74/471 |
| 5,389,865 A | 2/1995 | Jacobus et al. | 318/568.11 |
| 5,396,266 A | 3/1995 | Brimhall | 345/161 |
| 5,402,582 A | 4/1995 | Raab | 33/503 |
| 5,405,152 A | 4/1995 | Katanics et al. | 273/438 |
| 5,414,337 A | 5/1995 | Schuler | 318/561 |
| 5,436,640 A | 7/1995 | Reeves | 345/161 |
| 5,445,166 A | 8/1995 | Taylor | 128/897 |
| 5,473,235 A | 12/1995 | Lance et al. | 318/561 |
| 5,491,477 A | 2/1996 | Clark et al. | 341/20 |
| 5,513,100 A | 4/1996 | Parker et al. | 364/167.01 |
| 5,547,383 A | 8/1996 | Yamaguchi | 434/62 |
| 5,576,727 A | 11/1996 | Rosenberg et al. | 345/179 |
| 5,587,937 A | 12/1996 | Massie et al. | 364/578 |
| 5,589,828 A | 12/1996 | Armstrong | 341/20 |
| 5,589,854 A | 12/1996 | Tsai | 345/161 |
| 5,623,582 A | 4/1997 | Rosenberg | 395/99 |
| 5,629,594 A | 5/1997 | Jacobus et al. | 318/568.11 |
| 5,642,469 A | 6/1997 | Hannaford et al. | 395/99 |
| 5,643,087 A | 7/1997 | Marcus et al. | 463/38 |
| 5,666,138 A | 9/1997 | Culver | 345/161 |
| 5,709,219 A | 1/1998 | Chen et al. | 128/782 |
| 5,742,278 A | 4/1998 | Chen et al. | 345/156 |
| 5,769,640 A | 6/1998 | Jacobus et al. | 434/262 |
| 5,821,920 A | 10/1998 | Rosenberg et al. | 345/156 |

OTHER PUBLICATIONS

Ramstein, C. et al., "The Pantograph: A Large Workspace Haptic Device for a Multimodal Human—Computer Interaction," Computer—Human Interaction, CHI '94, pp. 1–3.

Payette, J. et al., "Evaluation of a Force Feedback (Haptic) Computer Pointing Device in Zero Gravity," DSC—vol. 58, Proceedings of the ASME Dynamics Systems and Control Division, ASME 1996, pp. 547–553.

Ramstein, Christophe, "Combining Haptic and Braille Technologies: Design Issues and Pilot Study," Assets '96, $2^{nd}$ Annual ACM Conf. on Assistive Technologies: Design Issues and Pilot Study, 1996, pp. 37–44.

Hayward, V. et al., "Design and Multi–Objective Optimization of a Linkage for a Haptic Interface," *Advances in Robot Kinematics and Computationed Geometry*, Kluwer Academic Publishers, 1994, pp. 359–368.

Millman, P. et al., "Design of a Four Degree–of–Freedom Force–Reflecting Manipulandum with a Specified Force/Torque Workspace," Proceedings of the 1991 IEEE Int'l Conf. on Robotics an Automation, 1991, pp. 1488–1493.

Tavkhelidze, D.S. et al., "Kinematic Analysis of Five–Link Spherical Mechanisms," *Mechanism and Machine Theory*, vol. 9, 1974, pp. 181–190.

Hirota, K. et al., "Development of Surface Display," IEEE 0–7803–1363, 1993, pp. 256–262.

Brooks, F. et al., "Project GROPE—Haptic Displays for Scientific Visualization," Computer Graphics, vol. 24, No. 4, 1990, pp. 177–185.

Iwata, Hiroo, "Artificial Reality with Force–feedback: Development of Desktop Virtual Space with Compact Master Manipulator," Computer Graphics, vol. 24, No. 4, 1990, pp. 165–170.

Iwata, H. et al., "Volume Haptization," IEEE 0–8186–4910–0/93, 1993, pp. 16–18.

Iwata, Hiroo, "Pen–based Haptic Virtual Environment," IEEE 0–7803–1363–1/93, 1993, pp. 287–292.

Snow, E. et al., "Compact Force–Reflecting Hand Controller," NASA Contract No. NAS 7–918, 1991.

McAffee, D. et al., "Teleoperator Subsystem/Telerobot Demonstrator Force Reflecting Hand Controller Equipment Manual," JPL D–5172, 1988.

Schmult, B. et al., "Application Areas for a Force–feedback Joystick," DSC—vol. 49, Advances in Robotics, Mechatronics, and Haptic Interfaces, ASME 1993, pp. 47–54.

Howe, R., "Task Performance with a Dextrous Teleoperated Hand System," Proceedings of SPIE, vol. 1833, 1992, pp. 1–9.

Rosenberg, L. et al., "Perceptual Decomposition of Virtual Haptic Surfaces," Proc. IEEE Symp. on Research Frontiers in Virtual Reality, 1993.

Rosenberg, L., "Virtual Haptic Overlays Enhance Performance in Telepresence Tasks," Stanford Univ., Dept. of Mech. Engineering, 1994.

Rosenberg, L., Virtual Fixtures as Tools to Enhance Operator Performance in Telepresence Environments, SPIE Telemanipulator Technology, 1993.

Ellis, R. E. et al., "Design and Evaluation of a High–Performance Prototype Planar Haptic Interface," DSC—vol. 49, Advances in Robotics, Mechatronics, and Haptic Interfaces, ASME 1993.

Bejczy, A. et al., "The Phantom Robot: Predictive Displays for Teleoperation with Time Delay," IEEE CH2876–1/90, 1990.

Colgate, J. et al., "Implementation of Stiff Virtual Walls in Force–Reflecting Interfaces," Dept. of Mech. Engineering, Northwestern Univ., 1993.

Hannaford, B. et al., "Performance Evaluation of a Six–Axis Generalized Force–Reflecting Teleoperator," IEEE Transactions on Systems, Man, and Cybernetics, vol. 21, No. 3, 1991.

Fischer, P., "Specification and Design of Input Devices for Teleoperation," IEEE CH2876–1/90, 1990.

Atkinson, W. et al., "Computing with Feeling," Comput. & Graphics, vol. 2.

Rosenberg, L., "The Use of Virtual Fixtures to Enhance Operator Performance in Time Delayed Teleoperation," Armstrong Laboratory, Crew Systems Directorate, Air Force Materiel Command, 1993.

Rosenberg, L., "Perceptual Design of a Virtual Rigid Surface Contact," Armstrong Laboratory, Crew Systems Directorate, Air Force Materiel Command, 1993.

Russo, M., "The Design and Implementation of a Three Degree–of–freedom Force Output Joystick," Dept. of Mech. Engineering, 1990.

Adelstein B. et al., "A High Performance Two Degree–of–Freedom Kinesthetic Interface,"Massachusetts Institute of Technology, 1992.

Batter, J. et al., "Grope–1: A Computer Display to the Sense of Feel," Proc. IFIP Congress, 1971.

Minsky, M. et al., "Feeling and Seeing: Issues in Force Display," ACM 089791–351–5, 1990.

Ouh–young, M. et al., "Force Display Performs Better than Visual Display in a Simple 6–D Docking Task," 1989 IEEE Int'l Conf. on Robotics and Automation, IEEE CH2750–8, 1989.

Jacobsen, S.C., "High Performance, High Dexterity, Force Reflective Teleoperator II," ANS Topical Meeting on Robotics and Remote Systems, 1991.

Kilpatrick, Paul, "The Use of Kinesthetic Supplement in an Interactive Graphics System," Univ. of North Carolina at Chapel Hill, 1976.

Herndon, J. N., "The State–of–the–Art Model M–2 Maintenance System," Proc. of 1984 Nat'l Topical Meeting on Robotics and Remote Handling in Hostile Environments, ANS, 1984.

Ouh–young, M., "Force Display in Molecular Docking," Univ. of North Carolina at Chapel Hill, 1990.

MECHANICAL AND FORCE TRANSMISSION FOR FORCE FEEDBACK DEVICES

CROSS REFERENCE TO RELATED APPLICATIONS

This application is a continuation-in-part of parent patent application Ser. No. 08/870,956, filed Jun. 6, 1997, now U.S. Pat. No. 6,246,390 entitled, "Method and Apparatus for Providing High Bandwidth, Low Noise Mechanical I/O for Computer Systems", which is a continuation of patent application Ser. No. 08/374,288, filed Jan. 18, 1995, now U.S. Pat. No. 5,731,804, assigned to the assignee of the present application, and which is incorporated by reference herein.

BACKGROUND OF THE INVENTION

The present invention relates generally to interface devices between humans and computers, and more particularly to computer interface devices that provide force feedback to the user.

Interface devices are used extensively with computer systems in the implementation of computer-controlled games, simulations, and other applications very popular with the mass market of home consumers. In a typical implementation, a computer system displays a visual environment to a user on a display device. Users can interact with the displayed environment by inputting commands or data from the interface device. Popular interface devices include joysticks, "joypad" button controllers, mice, trackballs, styluses, tablets, pressure spheres, foot or hand pedals, or the like, that are connected to the computer system controlling the displayed environment. The computer updates the environment in response to the user's manipulation of a moved manipulandum such as a joystick handle or mouse, and provides visual feedback to the user using the display screen.

In some interface devices, haptic (e.g., tactile) feedback is also provided to the user, more generally known as "force feedback." These types of interface devices can provide physical sensations to the user manipulating the physical object of the interface device. Typically, motors or other actuators of the interface device are coupled to the manipulandum and are connected to the controlling computer system. The computer system receives sensor signals from the interface device and sends appropriate force feedback control signals to the actuators in conjunction with host events. The actuators then provide forces on the manipulandum. A local microprocessor can be used to offload some computational burden on the host. The computer system can thus convey physical sensations to the user in conjunction with other visual and auditory feedback as the user is contacting the manipulandum. Commercially available force feedback devices include the ForceFX joystick from CH Products, Inc. and Immersion Corporation, and the Sidewinder Force Feedback Pro from Microsoft Corporation.

One problem occurring in the commercially available force feedback devices is that the motion transmission mechanisms in these devices are typically not ideal for transmitting forces. Well known motion transmission mechanisms such as a slotted bail tend to induce more friction and backlash than is desirable for conveying realistic and subtle force sensations. This limits the degree of sensitivity conveyed to the user through the actuators of the device, and as a result the user feels force sensations on such devices as less precise, immersive, and meaningful.

A different problem occurring in providing commercially available force feedback devices with realistic forces is providing a low cost device. Force feedback components, such as the transmission, tend to incur a large portion of the cost of manufacturing the device. For example, cable drives or capstan drives can offer high-bandwidth, amplified forces but are typically difficult to assemble, thus causing higher expense. Belt drives, in contrast, are typically easier to assemble and thus can provide amplified forces at a lower cost of production. However, belt drives that use tension or preload in the belt to transmit forces typically introduce a significant amount of friction and thus can be unsuitable for use in a force feedback device.

Non-tensioned belt drives do not use tension but instead engage the belt with pulleys using teeth or other positive grip elements, and thus have much less friction and are much more suitable for use in a force feedback device than tensioned belt drives. However, one problem occurring with the non-tensioned type of belt drives is that an amount of compliance is typically inherent in the system caused by slack in the belts. This slack can sometimes cause the belts to slip off or jump radially away from the drive pulleys or other pulleys in the drive system, causing loss of positive engagement and a concomitant loss in quality of force sensations. It can be a problem to prevent this movement and slippage without increasing the friction in the system.

SUMMARY OF THE INVENTION

The present invention provides a force feedback interface device which includes several improvements to the mechanical and force transmission system. One feature is the linkage mechanism disclosed herein that provides minimal backlash, friction, and compliance and allows the actuators of the system to be grounded. Other features include a belt drive mechanism including features to reduce the probability of the belt jumping off the drive mechanism.

More particularly, in one embodiment, a force feedback device of the present invention is coupled to a host computer and includes a user manipulatable object graspable by a user, two actuators operative to output a force in provided degrees of freedom, and at least one sensor operative to sense motion of the user manipulatable object in the degrees of freedom and which can be coupled to the actuators. A linkage mechanism is coupled between the actuators and the user object and provides the user object with first and second rotary degrees of freedom. The linkage mechanism includes a grounded member, a first extension member and a second extension member rotatably coupled to the grounded member, and a first central member rotatably coupled to the first extension member and a second central member rotatably coupled to the second extension member. The first and second central members are rotatably coupled to each other, and the first extension member and first central member are substantially identical to and positioned symmetrically to the second extension member and second central member.

The first and second extension members each preferably include two protrusions, where each of the protrusions is rotatably coupled to the first and second central members, respectively. Portions of the first and second extension members extend out of a plane formed by axes of rotation for the first and second degrees of freedom, where the portions that extend out of the plane are preferably a middle portion of at least one of the protrusions. At least one protrusion of the first extension member extends out of the plane on a first side of the plane, and at least one protrusion of the second extension member extends out of the plane on a second side of the plane opposite to the first side. The protrusions of the first extension member are rotatably coupled to the first central member such that the first central member is positioned between the protrusions, and a similar arrangement is provided for the second extension and central members. Some or all portions of the linkage mechanism and the drive mechanism, such as a belt drive, are preferably symmetrical and thus allows low cost manufacture of the device.

In a different aspect of the present invention, a force feedback device is coupled to a host computer and includes a user manipulatable object graspable by a user and moveable in at least one degree of freedom, at least one sensor operative to sense motion of the user object, and an actuator for outputting a force on the user object. A belt drive transmission is coupled between the actuator and the user object, and the belt drive transmission includes a drive pulley coupled to the actuator, an amplification pulley coupled to the drive pulley by a preferably synchronous belt, and an idler positioned adjacent to the drive pulley. The idler impedes radial displacement of the belt away from the drive pulley during normal operation without preloading the belt. The idler preferably is provided as two different types, a passive idler and an active idler. The passive idler does not contact the belt during operation, thus providing no friction, and prevents the belt from moving a significant amount radially off the drive pulley and losing engagement when the belt is so influenced due to slack or compliance in the belt. The active idler continually contacts the belt during normal operation and increases the wrap angle of the belt on the drive pulley to prevent the jumping of the belt as well as slippage. In a two-stage embodiment, one or more passive idlers can be included in the first stage of the belt drive transmission, and one or more active idlers can be included in the second stage. Both stages can include amplification pulleys to amplify the forces output by the actuator, where the first stage is provided between the actuator and the second stage.

The improvements of the present invention provide a more precise and quality force feedback device, yet also allow the device to be manufactured at a significantly lower cost for competitive consumer markets. Both the linkage mechanism and belt drive transmission provide high bandwidth, low friction, and low compliance and permit force sensations to be transmitted with high fidelity from grounded actuators. The linkage mechanism provides enhanced support of couplings moved during use of the device. The belt drive improvements also allow for a belt drive transmission that is more easily manufactured without introducing problems occurring with the belt drive due to slack in the belt. Furthermore, the device has many symmetrical components that can be duplicated and reused to create a functional device at a much lower cost.

These and other advantages of the present invention will become apparent to those skilled in the art upon a reading of the following specification of the invention and a study of the several figures of the drawing.

DETAILED DESCRIPTION OF PREFERRED EMBODIMENTS

Figure 1:
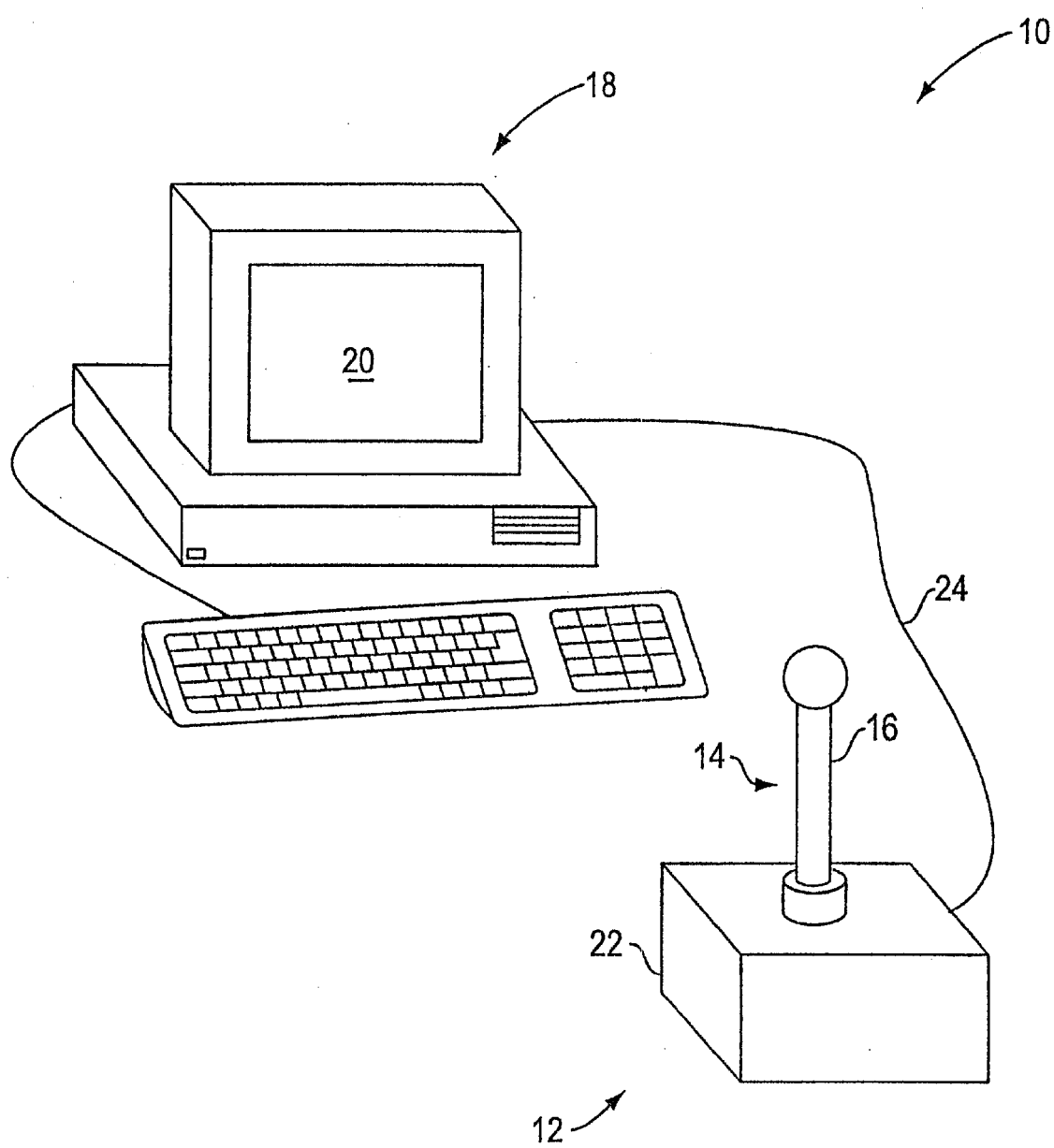
FIG. 1 is a perspective view of a force feedback system which includes a host computer and a force feedback interface device.

In FIG. 1, a force feedback system 10 includes a force feedback interface device 12 and a host computer 18. The illustrated system 10 can be used for a virtual reality simulation, computer/video game, training procedure or simulation, computer application program, or other application. In one preferred embodiment, a user manipulatable object 14 is grasped by a user and manipulated in one or more degrees of freedom of motion. Images are displayed on a display apparatus, such as screen 20, of the computer 18 in response to such manipulations.

The computer 18 can be a personal computer or workstation, such as an IBM-PC compatible computer, Macintosh personal computer, or a SUN or Silicon Graphics workstation. Most commonly, the digital processing system is a personal or portable computer which operates under the Windows™, Unix, MacOS, or other operating system and may include a host microprocessor such as a Pentium class microprocessor, PowerPC, DEC Alpha, or other type of microprocessor. Alternatively, host computer system 18 can be one of a variety of home video game systems commonly connected to a television set, such as systems available from Nintendo, Sega, or Sony. In other embodiments, host computer system 18 can be a "set top box" which can be used, for example, to provide interactive television functions to users, or a "network-" or "internet-computer" which allows users to interact with a local or global network using standard connections and protocols such as used for the Internet and World Wide Web.

Host computer 18 preferably implements a host application program with which a user is interacting via user object 14 and other peripherals, if appropriate, and which can include force feedback functionality. The software running on the host computer 18 may be of a wide variety. For example, the host application program can be a simulation, video game, Web page or browser that implements HTML or VRML instructions, scientific analysis program, virtual reality training program or application, or other application program that utilizes input of user object 14 and outputs force feedback commands to the user object 14. For example, many game application programs include force feedback functionality and may communicate with the force feedback interface device 12 using a standard protocol/drivers such as I-Force available from Immersion Corporation. Herein, computer 18 may be referred as displaying "graphical objects" or "computer objects." These objects are not physical objects, but are logical software unit collections of data and/or procedures that may be displayed as images by computer 18 on display screen 20, as is well known to those skilled in the art. A displayed cursor or a simulated cockpit of an aircraft might be considered a graphical object.

Display device 20 can be included in host computer 18 and can be a standard display screen (LCD, CRT, etc.), 3-D goggles, or any other visual output device. Typically, the host application provides images to be displayed on display device 20 and/or other feedback, such as auditory signals. For example, display screen 20 can display images from a game program.

The interface device 12 as illustrated in FIG. 1 is used to provide an interface to the application running on host computer 18. For example, a user manipulatable object (or "manipulandum") 14 grasped by the user in operating the device 12 may be a joystick handle 16 movable in one or more degrees of freedom, as described in greater detail subsequently. It will be appreciated that a great number of other types of user objects can be used with the method and apparatus of the present invention. In fact, the present invention can be used with any mechanical object where it is desirable to provide a human/computer interface with two to six degrees of freedom. Such objects may include joysticks, styluses, surgical tools used in medical procedures, catheters, hypodermic needles, wires, fiber optic bundles, screw drivers, pool cues, etc.

A housing 22 of the interface device 12 holds a mechanical apparatus for interfacing mechanical input and output. The mechanical apparatus mechanically provides the degrees of freedom available to the user object 16 and allows sensors to sense movement in those degrees of freedom and actuators to provide forces in those degrees of freedom. The mechanical apparatus is described in greater detail below. The mechanical apparatus is adapted to provide data from which a computer or other computing device such as a microprocessor (see FIG. 2) can ascertain the position and/or orientation of the user object as it moves in space. This information is then translated to an image on a computer display apparatus such as screen 20. The mechanical apparatus may be used, for example, by a user to change the position of a user controlled graphical object on display screen 20 by changing the position and/or orientation of the user object 14, the computer 18 being programmed to change the position of the graphical object in proportion to the change in position and/or orientation of the user object (or according to some other relationship). In other words, the user object is moved through space by the user which indicates to the computer how to update the implemented program.

An electronic interface is also included in housing 22 of interface device 12. The electronic interface couples the device 12 to the computer 18. More particularly, the electronic interface is used in preferred embodiments to couple the various actuators and sensors contained in device 12 (which actuators and sensors are described in detail below) to computer 18. A suitable electronic interface is described in detail with reference to FIG. 2. The electronic interface is coupled to a mechanical apparatus within the interface device 12 and to the computer 18 by a cable 24. In other embodiments, signals can be transmitted between interface device 12 and computer 18 by wireless transmission and reception.

Figure 2:
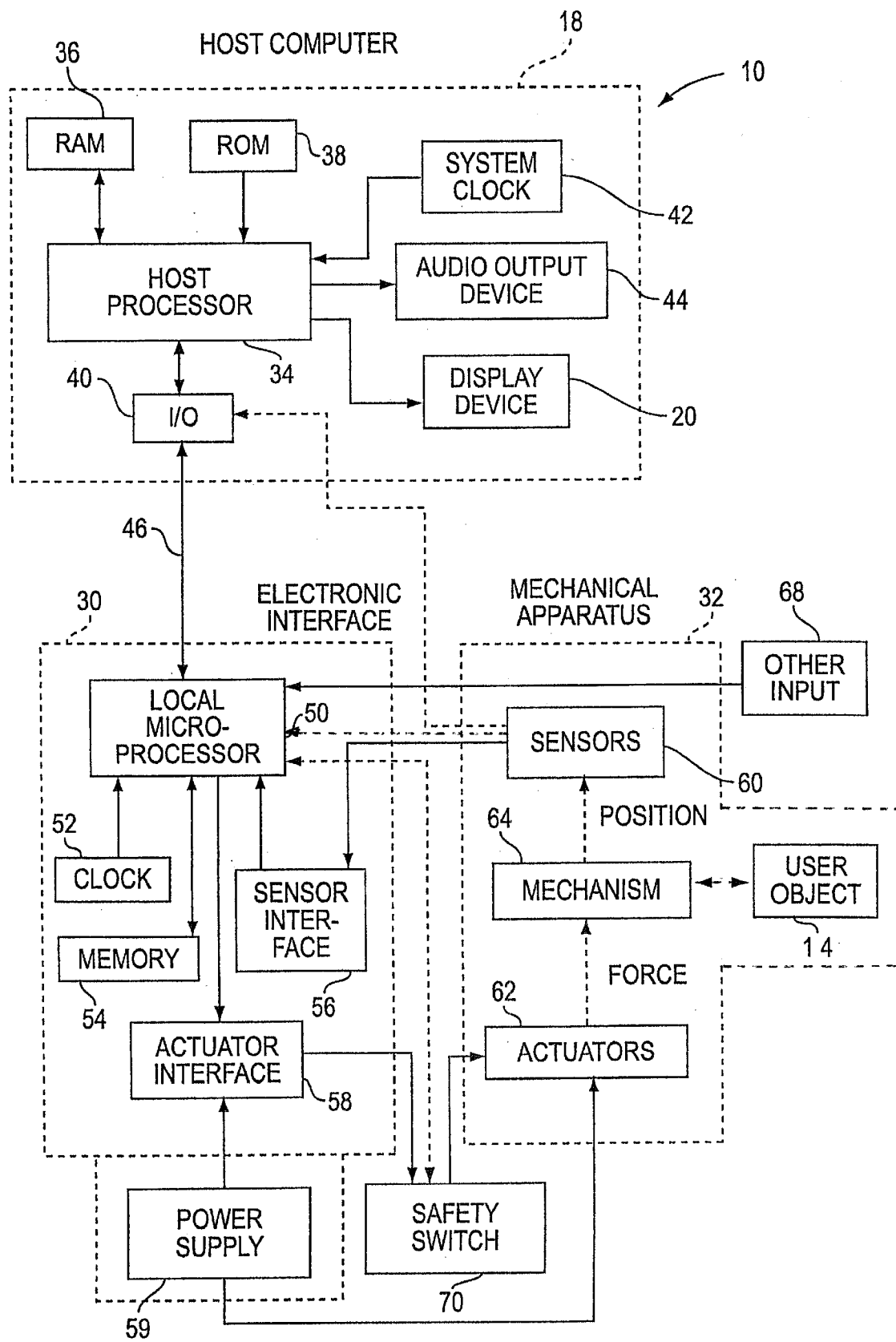
FIG. 2 is a block diagram of the force feedback system of FIG. 1.

FIG. 2 is a block diagram illustrating interface device 12 and host computer 18 suitable for use with the present invention. Interface device 12 includes an electronic interface 30, mechanical apparatus 32, and user object 14. A similar system is described in detail in U.S. Pat. No. 5,734,373 which is hereby incorporated by reference herein in its entirety.

As explained with reference to FIG. 1, computer 18 is preferably a personal computer, workstation, video game console, or other computing or display device. Host computer system 18 commonly includes a host microprocessor 34, random access memory (RAM) 36, read-only memory (ROM) 38, input/output (I/O) electronics 40, a clock 42, a display device 20, and an audio output device 44. Host microprocessor 34 can include a variety of available microprocessors from Intel, AMD, Motorola, or other manufacturers. Microprocessor 34 can be single microprocessor chip, or can include multiple primary and/or co-processors and preferably retrieves and stores instructions and other necessary data from RAM 36 and ROM 38 as is well known to those skilled in the art. In the described embodiment, host computer system 18 can receive sensor data or a sensor signal via a bus 46 from sensors of device 12 and other information. Microprocessor 34 can receive data from bus 46 using I/O electronics 40, and can use I/O electronics to control other peripheral devices. Host computer system 18 can also output commands to interface device 12 via bus 46 to cause force feedback for the interface system 10.

Clock 42 is a standard clock crystal or equivalent component used by host computer 18 to provide timing to electrical signals used by host microprocessor 34 and other components of the computer system 18 and can be used to provide timing information that may be necessary in determining force or position values. Display device 20 is described with reference to FIG. 1. Audio output device 44, such as speakers, can be coupled to host microprocessor 34 via amplifiers, filters, and other circuitry well known to those skilled in the art. Other types of peripherals can also be coupled to host processor 34, such as storage devices (hard disk drive, CD ROM drive, floppy disk drive, etc.), printers, and other input and output devices.

Electronic interface 30 is coupled to host computer system 18 by a bi-directional bus 46. The bi-directional bus sends signals in either direction between host computer system 18 and the interface device 12. Bus 46 can be a serial interface bus, such as USB, RS-232, or Firewire (IEEE 1394), providing data according to a serial communication protocol, a parallel bus using a parallel protocol, or other types of buses. An interface port of host computer system 18, such as a USB or RS232 serial interface port, connects bus 46 to host computer system 18.

Electronic interface 30 includes a local microprocessor 50, local clock 52, local memory 54, sensor interface 56, and actuator interface 58. Interface 30 may also include additional electronic components for communicating via standard protocols on bus 46. In various embodiments, electronic interface 30 can be included in mechanical apparatus 32, in host computer 18, or in its own separate housing. Different components of interface 30 can be included in device 12 or host computer 18 if desired.

Local microprocessor 50 is preferably coupled to bus 46 and may be closely linked to mechanical apparatus 14 to allow quick communication with other components of the interface device. Processor 50 is considered "local" to interface device 12, where "local" herein refers to processor 50 being a separate microprocessor from any processors 34 in host computer 18. "Local" also preferably refers to processor 50 being dedicated to force feedback and sensor I/O of the interface system 10, and being closely coupled to sensors and actuators of the device 12, such as within the housing of or in a housing coupled closely to device 12. Microprocessor 50 can be provided with software instructions to wait for commands or requests from computer host 18, parse/decode the command or request, and handle/control input and output signals according to the command or request. In addition, processor 50 preferably operates independently of host computer 18 by reading sensor signals and calculating appropriate forces from those sensor signals, time signals, and force processes selected in accordance with a host command, and output appropriate control signals to the actuators. Suitable microprocessors for use as local microprocessor 50 include the 8X930AX by Intel, the MC68HC711E9 by Motorola or the PIC16C74 by Microchip, for example. Microprocessor 50 can include one microprocessor chip, or multiple processors and/or co-processor chips. In other embodiments, microprocessor 50 can include digital signal processor (DSP) functionality.

For example, in one host-controlled embodiment that utilizes microprocessor 50, host computer 18 can provide low-level force commands over bus 46, which microprocessor 50 directly transmits to the actuators. In a different local control embodiment, host computer system 18 provides high level supervisory commands to microprocessor 50 over bus 46, and microprocessor 50 manages low level force control loops to sensors and actuators in accordance with the high level commands and independently of the host computer 18. In the local control embodiment, the microprocessor 50 can process inputted sensor signals to determine appropriate output actuator signals by following the instructions of a "force process" that may be stored in local memory 54 and includes calculation instructions, formulas, force magnitudes, or other data. The force process can command distinct force sensations, such as vibrations, textures, jolts, or even simulated interactions between displayed objects. For instance, the host can send the local processor 50 a spatial layout of objects in the graphical environment so that the microprocessor has a mapping of locations of graphical objects and can determine force interactions locally. Force feedback used in such embodiments is described in greater detail in co-pending patent application Ser. No. 08/879,296 and U.S. Pat. No. 5,734,373, both of which are incorporated by reference herein.

A local clock 52 can be coupled to the microprocessor 50 to provide timing data, similar to system clock 42 of host computer 18; the timing data might be required, for example, to compute forces output by actuators 30. Local memory 54, such as RAM and/or ROM, is preferably coupled to microprocessor 50 in interface 30 to store instructions for microprocessor 50 and store temporary and other data. Microprocessor 50 may also store calibration parameters and the state of the force feedback device in a local memory 54.

Sensor interface 56 may optionally be included in electronic interface 30 to convert sensor signals to signals that can be interpreted by the microprocessor 50 and/or host computer system 18. For example, sensor interface 56 can receive and convert signals from a digital sensor such as an encoder or from an analog sensor using an analog to digital converter (ADC). Such circuits, or equivalent circuits, are well known to those skilled in the art. Alternately, microprocessor 50 can perform these interface functions or sensor signals from the sensors can be provided directly to host computer system 18. Actuator interface 58 can be optionally connected between the actuators of device 12 and microprocessor 50 to convert signals from microprocessor 50 into signals appropriate to drive the actuators. Interface 58 can include power amplifiers, switches, digital to analog controllers (DACs), and other components well known to those skilled in the art.

Power supply 59 can optionally be coupled to actuator interface 58 and/or actuators 62 to provide electrical power. Active actuators typically require a separate power source to be driven. Power supply 59 can be included within the housing of interface device 12, or can be provided as a separate component, for example, connected by an electrical power cord. Alternatively, if the USB or a similar communication protocol is used, actuators and other components can draw power from the USB from the host computer. Alternatively, power can be stored and regulated by interface device 12 and thus used when needed to drive actuators 62.

Mechanical apparatus 32 is coupled to electronic interface 30 and preferably includes sensors 60, actuators 62, and mechanism 64. Sensors 60 sense the position, motion, and/or other characteristics of a user object 14 along one or more degrees of freedom and provide signals to sensor interface 56 or microprocessor 50 including information representative of those characteristics. Typically, a sensor 60 is provided for each degree of freedom along which object 14 can be moved, or, a single compound sensor can be used for multiple degrees of freedom. Example of sensors suitable for embodiments described herein are digital rotary optical encoders, which sense the change in position of an object about a rotational axis and provide digital signals indicative of the change in position. Linear optical encoders may similarly sense the change in position of object 14 along a linear degree of freedom. A suitable optical encoder is the "Softpot" from U.S. Digital of Vancouver, Washington. Alternatively, analog sensors such as potentiometers can be used. It is also possible to use non-contact sensors at different positions relative to mechanical apparatus 32, such as Polhemus (magnetic) sensors for detecting magnetic fields from objects, or an optical sensor such as a lateral effect photo diode having an emitter/detector pair. In addition, velocity sensors (e.g., tachometers) and/or acceleration sensors (e.g., accelerometers) can be used. Furthermore, either relative or absolute sensors can be employed.

Actuators 62 transmit forces to user object 14 in one or more directions along one or more degrees of freedom in response to signals output by microprocessor 50 and/or host computer 18, i.e., they are "computer controlled." Typically, an actuator 62 is provided for each degree of freedom along which forces are desired to be transmitted. Actuators 62 can include two types: active actuators and passive actuators. Active actuators include linear current control motors, stepper motors, pneumatic/hydraulic active actuators, a torquer (motor with limited angular range), a voice coil actuator, and other types of actuators that transmit a force to an object. Passive actuators can also be used for actuators 62, such as magnetic particle brakes, friction brakes, or pneumatic/hydraulic passive actuators, and generate a damping resistance or friction in a degree of motion. In some embodiments, all or some of sensors 60 and actuators 62 can be included together as a sensor/actuator pair transducer.

Figure 3:
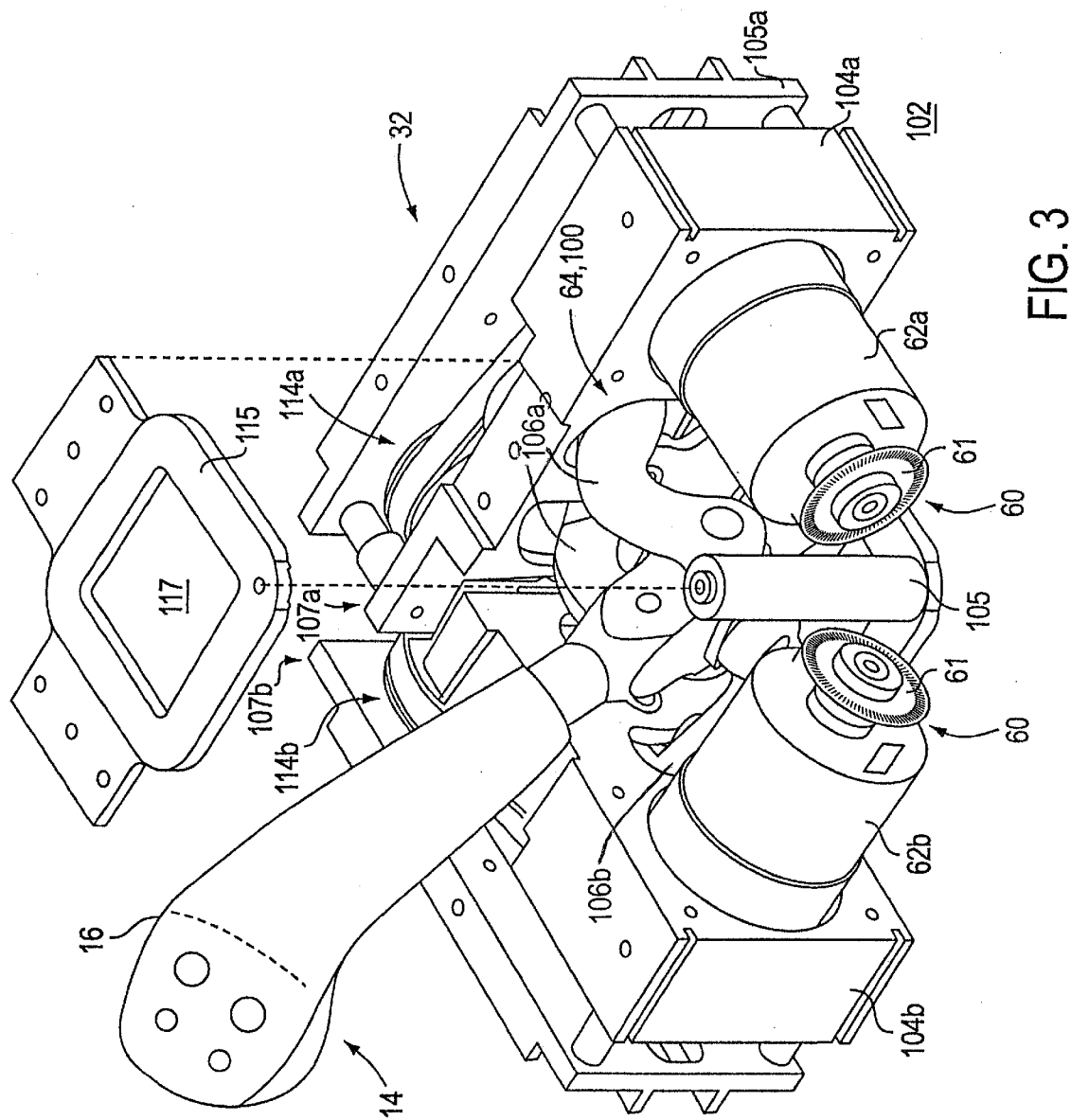
FIG. 3 is a perspective view of a preferred embodiment of the force feedback interface device of FIG. 2.
Figure 4:
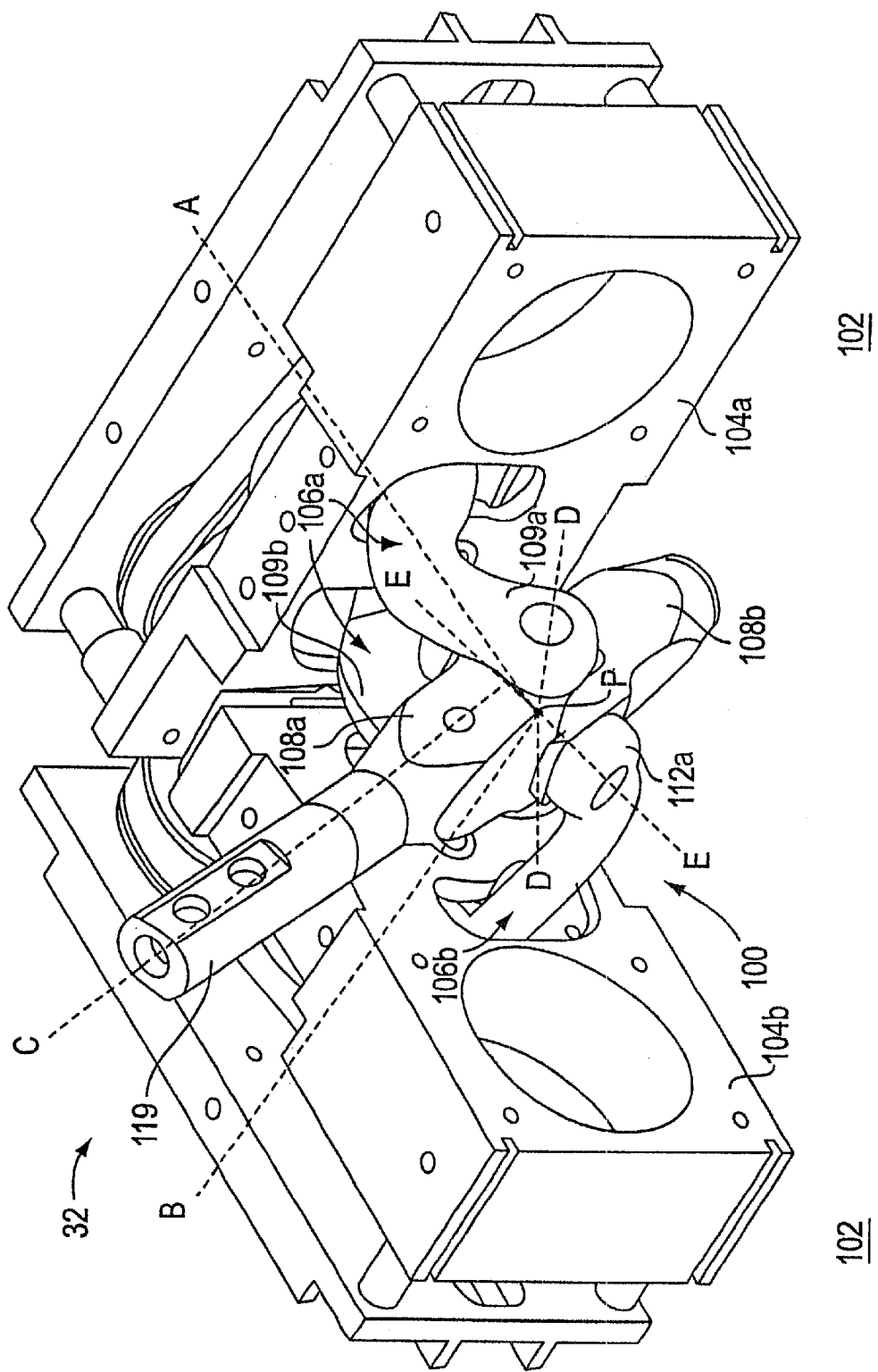
FIG. 4 is a perspective view of the embodiment of the force feedback interface device of FIG. 3 detailing the linkage mechanism of the device.

Mechanism 64 can be one of several types of mechanisms. A preferred mechanism is shown in FIGS. 3-4. Other mechanisms may also be used (e.g. with the belt drive of the present invention), such as mechanisms and related features disclosed in U.S. Pat. Nos. 5,576,727; 5,731,804; 5,721,566; 5,691,898, and 5,767,839 and co-pending patent applications Ser. Nos. 08/560,091, 08/664,086, 08/709,012, 08/736,161, 08/881,691, 08/961,790, 08/965,720, and 09/058,259, all hereby incorporated by reference herein in their entirety. User object 14 can be a joystick, or other device or article coupled to mechanism 64, as described above.

Other input devices 68 can optionally be included in interface system 10 and send input signals to microprocessor 50 and/or host computer 18. Such input devices can include buttons, such as buttons on joystick handle 16, used to supplement the input from the user to a game, simulation, GUI, etc. Also, dials, switches, voice recognition hardware (with software implemented by host 18), or other input mechanisms can be used.

Safety or "deadman" switch 70 is preferably included in the interface device to provide a mechanism to allow a user to override and deactivate actuators 62, or require a user to activate actuators 62, for safety reasons. For example, the user must continually activate or close safety switch 70 during manipulation of user object 14 to activate the actuators 62. If, at any time, the safety switch is deactivated (opened), power from power supply 59 is cut to actuators 62 (or the actuators are otherwise deactivated) as long as the safety switch is deactivated. Embodiments of safety switch 70 include an optical safety switch, electrostatic contact switch, hand weight safety switch, etc. The safety switch can also be implemented in firmware or software for microprocessor 50.

FIG. 3 is a perspective view of one embodiment of the mechanical portion 32 and user object 14 of interface device 12 and including the features of the present invention. The described embodiment is a joystick apparatus including two rotary degrees of freedom, where a joystick handle 16 can be moved forward and back in one degree of freedom, and left and right in the other degree of freedom.

Mechanism 64 is provided as a gimbal mechanism 100 which couples the user object 14 to a grounded or reference surface 102. Gimbal mechanism 100 is preferably a five-member, closed-loop parallel linkage and is described in greater detail below with reference to FIG. 4. Gimbal mechanism 100 provides two degrees of freedom to handle 16. Joystick handle 16 is coupled to one of the members of gimbal mechanism 100 such that it extends out of the sphere defined by the rotational degrees of freedom of the handle 16.

Mechanical apparatus also includes belt drive mechanisms 114a and 114b. Belt drive mechanisms 114 are included in mechanical portion 32 to provide mechanical advantage to the output of actuators 62 without introducing as much backlash into the system as other types of transmission systems. The belt drive mechanisms 114 are described in greater detail with respect to FIG. 7. The gimbal mechanism 100 can alternatively be used with other types of drive amplification transmissions, such as a gear system or a capstan drive mechanism as described in parent U.S. Pat. No. 5,731,804.

Also preferably coupled to mechanical portion 32 are sensors 60 and actuators 62 and provide input to and output from the electrical system. Such transducers, in the described embodiment, are coupled such that the belt drive is positioned between the sensor/actuator and the gimbal mechanism 100; the transducers can be coupled elsewhere in other embodiments. Transducers that can be used with the present invention are described in greater detail with respect to FIG. 2. In the described embodiment, actuators 62 include two grounded actuators 62a and 62b. The housing of grounded actuator 62a is preferably coupled to ground member 104. A rotational shaft (rotor) of actuator 62a is coupled to the belt drive mechanism 114a to apply forces to the joystick handle 16 in a first revolute degree of freedom (linear actuators can be provided in alternate embodiments). The belt drive mechanisms 114 are described in greater detail with respect to FIG. 7. Grounded actuator 62b preferably corresponds to grounded transducer 62a in function and operation, where actuator 62b is coupled to the grounded member 104 and applies forces to the joystick handle 16 in the second revolute degree of freedom.

Actuators 62, in the described embodiment, are preferably linear current control motors, such as DC servo motors. These motors preferably receive current signals to control the direction and torque (force output) that is produced on a rotor; the control signals for the motor are produced by microprocessor 50 as explained above. Such motors typically operate at stall in a force feedback device to transmit the forces to the user object grasped by the user. The motors may include brakes which allow the rotation of the rotor to be halted in a short span of time. A suitable motor to be used as actuators 62 is the 600LG series manufactured by Johnson Electric. In alternate embodiments, other types of motors or actuators can be used, such as a stepper motor controlled with pulse width modulation of an applied voltage, pneumatic/hydraulic motors, voice coil actuators, or passive actuators (magnetic particle brakes, pneumatic/hydraulic passive brakes, etc).

The actuators 62 of the described embodiment are advantageously positioned to provide a very low amount of inertia to the joystick handle 16. Actuators 62 are decoupled, meaning that the transducers are both directly coupled to ground member 104 which is coupled to ground surface 102, i.e. the ground surface carries the weight of the actuators, not the joystick handle 16. The weights and inertia of the actuators 62 are thus substantially negligible to a user handling and moving handle 16. This allows more realistic forces to be transmitted to user object 14.

It should be noted that the rotatable components of the mechanical portion 32 will only actually rotate in space if the user is not applying the same amount of rotational force to handle 16 in the opposite direction to cancel the rotational force of the actuator. In this case, either the force of the user or the force from the actuators 62 will move the user object and coupled components in their respective degrees of freedom. In any event, the user will feel the rotational force from the actuators 62 along the associated degree of freedom on handle 16 as force feedback.

Sensors 60 are, in the described embodiment, coupled to the actuators 62a and 62b. One portion of the sensor is grounded by being coupled to the housing of the actuator 62, which is itself grounded. A rotary shaft or encoder wheel of each sensor is rigidly coupled to the rotor of the corresponding actuator 62, such that the sensor detects any motion caused by the output force of the actuator. The sensors 60 also detect any rotary motion of the rotor caused by the user moving the joystick 16. For example, in the described embodiment, sensors 60 are relative optical encoders which provide signals to measure the angular rotation of a shaft of the sensor. An encoder wheel 61 can be provided on the shaft with a number of slots. A beam emitter and a detector are positioned on opposing sides of the encoder wheel to detect the number of slots that have rotated past the detector, so that the rotation of the wheel is detected. The operation of such encoders are well known to those skilled in the art. The electrical outputs of the encoders are routed to microprocessor 50 (or host computer 18) as detailed above. Other types of sensors can also be used, such as potentiometers or other analog or digital sensors as described above. It should be noted that the present invention can utilize both absolute and relative sensors.

In the described embodiment of the present invention, the sensors 60 are preferably coupled directly to the rotors of actuators 62 such that the belt drive is positioned between the sensor/actuator and the gimbal mechanism 100. This allows the sensor to detect an amplified rotation of the user object 14 caused by the belt drive and effectively provide a higher sensing resolution, e.g. the belt drive amplifies the rotation of the user object 14, enabling a higher resolution reading with the same number of slots in an encoder wheel of the sensor. Other advantages of providing a sensor coupled to the actuator include the opportunity to use a smaller housing 22 and a convenient layout of components to allow efficient placement of the sensors. For example, the two sensors 60 can be placed close to each other at the ends of actuators 62 on a printed circuit board positioned between the actuators 62. In addition, the mechanism of the present invention is suitable for use with compliance compensation and accurate position sensing features disclosed in copending patent application Ser. No. 09/138,309, entitled, "Improvements in Position Sensing for Force Feedback Devices"," by Braun et al., filed concurrently herewith, and incorporated herein by reference.

In an alternate embodiment, each sensor can be coupled to a pulley of the belt drive mechanism 114 to measure the rotation of the pulley. If the sensor is coupled to an intermediate pulley (not an output pulley), such an embodiment will also have the advantage of increasing sensor resolution since the intermediate pulley rotates more than one rotation for each rotation of the extension member. However, the resolution in such an embodiment tends to be inferior to that of the preferred embodiment. The sensors 60 can also be directly coupled to a moving member of the gimbal mechanism to directly measure motion of the user object 14, e.g. when using potentiometers that do not improve sensing with amplified motion.

A distinct feature of the embodiment of the present invention shown in FIG. 3 is that the device is substantially symmetrical in many of its components, i.e., one half of the device is substantially identical to the other half of the device. For example, the extension member 106a the grounded member 104a, the belt drive mechanism 114a, actuator 62a, and the sensor 60a are all preferably identical to their corresponding components 106b, 104b, 114b, 62b, and 60b. The grounded member 104a is shaped so that when it is duplicated as grounded member 104b and rotated/positioned appropriately, ground member 104b attaches at the ends 107a of ground member 104a at its own ends 107b (as more clearly shown in FIG. 7) and provides coupling locations for extension member 106b and actuator 62b at the appropriate locations symmetrical to the locations on ground member 104a. Thus, one half of the device, including extension member 106a, grounded member 104a, belt drive assembly 114a, actuator 62a, and sensor 60a, can be duplicated exactly and the resulting components can be joined together as shown in FIG. 3 to complete the device. This can provide substantial savings in the manufacturing process since there are substantially less unique parts required in manufacturing with their own molds, part numbers, stock locations, etc.

A plate 115 is also shown in FIG. 3 which is shown in an exploded view above its normal connected position to grounded member 104 and a grounded post 105. Plate 115 includes an aperture 117 through which the joystick handle 16 normally extends. The limits of aperture 117 acts as hard stops to the motion of the joystick 16 and members 108a and 108b in the two rotary degrees of freedom. A second similar plate (not shown) to plate 115 or fence (or other obstruction) can also be provided at the bottom of the device for providing hard stops for a portion of joystick 16 which extends to the bottom of the device. Hard stops can be located in other areas of the device in other embodiments, such as on or near the gimbal mechanism 100.

Figure 5:
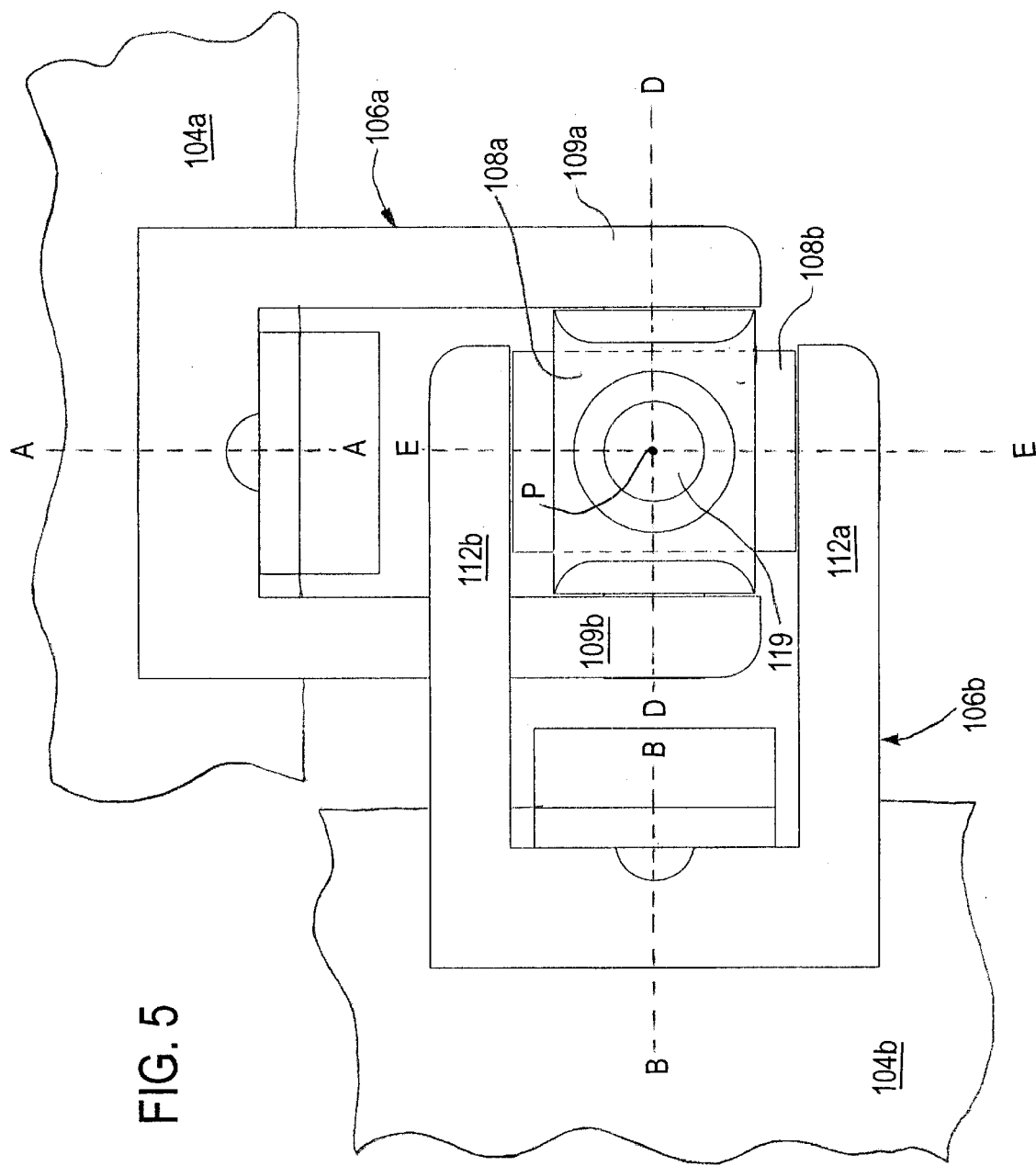
FIG. 5 is a top plan view of the linkage mechanism of the present invention shown in FIG. 4.

FIG. 4 is a perspective view of the mechanical portion 32 of interface device 12 detailing the gimbal mechanism 100. Gimbal mechanism 100 couples the user object 14 to a grounded or reference surface 102. All or some of the components of gimbal mechanism 100 (and other components) can be made of metal, or, in a preferred low-cost embodiment, rigid plastic. Gimbal mechanism 100 is preferably a five-member, closed-loop parallel linkage that includes a ground member 104, extension members 106a and 106b, and central members 108a and 108b. Ground member 104 is provided as a base member which provides stability for device 12 on a grounded surface 102, such as a table top, floor, desk top, or other reference surface (grounded member 104 is shown as members 104a and 104b, which are both directly coupled to ground 102). The members of gimbal mechanism 100 are rotatably coupled to one another through the use of bearings or pivots, wherein extension member 106a is rotatably coupled to ground member 104 and can rotate about an axis A, central member 108a is rotatably coupled to extension member 106a and can rotate about a floating axis D, extension member 106b is rotatably coupled to ground member 104 and can rotate about axis B, central member 108b is rotatably coupled to extension member 106b and can rotate about floating axis E, and central member 108a is rotatably coupled to central member 108b at or near a center point P at the intersection of axes D and E. A bearing (see FIG. 6) connects the two central members 108a and 108b together near the intersection point P of axes D and E. Central drive member 108a is rotatably coupled between two protrusions 109a and 109b of extension member 106a. Similarly, central link member 108b is rotatably coupled between two protrusions 112a and 112b of extension member 106b. The axes D and E are "floating" in the sense that they are not fixed in one position as are axes A and B. Axes A and B are substantially mutually perpendicular. The connection and relative position of the members of gimbal mechanism 100 is also shown in the top plan view of FIG. 5.

Gimbal mechanism 100 is formed as a five-member ("five-bar") closed chain. Each end of one member is coupled to the end of another member. The five-bar linkage is arranged such that extension member 106a, central member 108a, and central member 108b can be rotated about axis A in a first degree of freedom. The linkage is also arranged such that extension member 106b, central member 108b, and central member 108a can be rotated about axis B in a second degree of freedom. A similar structure is also disclosed in parent U.S. Pat. No. 5,731,804, which is incorporated by reference herein.

The protrusions 109 and 112 of the present invention are advantageous in that they allow more stability for the user object 14. Since each extension member 106 supports a central member 108 positioned between the protrusions of the extension member, there are two bearing supports for each extension member. Thus, there is less load and therefore less wear on these bearings and less deflection of extension member 106 since any weight is more evenly distributed over the two protrusions/bearings than when the extension member 106 is coupled with only one bearing on one side of the central member 108. In addition, the dual bearing supports allow for substantially larger manufacturing tolerances, as would be expected with plastics, without sacrificing stability and ultimately force and motion fidelity.

The protrusions 109 and 112 of the extension members 106 are also preferably bent in shape as shown in FIG. 4. The extension members 106 are preferably bent out of the plane formed by the axes of rotation A and B, where one extension member 106a is bent in one direction out of the plane and the other extension member 106b is bent in the opposite direction. Thus, extension member 106a includes protrusions 109a and 109b which first bend away from the AB plane and point P and then extend back toward center point P. Protrusions 112a and 112b bend away from and then toward the AB plane of center point P on the opposite side of the horizontal plane of point P from the protrusions 109. This bent configuration allows the central members 108 to be positioned between the two sets of protrusions 109 and 112 of each extension member without the protrusions of different members interfering with each other in physical space, and thus allows the dual bearing supports to be implemented with the associated advantages.

In an alternate embodiment, one of the protrusions of each of the extension members bends in the opposite direction to the other protrusion of that extension member; for example, the inner protrusion 109b bends in one direction out of plane AB and the outer protrusion 109a bends in the opposite direction out of plane AB. In such an embodiment, the inner protrusion 112b should bend in the opposite direction from inner protrusion 109b. In other embodiments, only the inner protrusions 109b and 112b of each extension member bends out of the plane AB in opposite directions to each other, while outer protrusions 109a and 112a of each extension member can be oriented in any shape or direction, such as substantially linearly. This can be accomplished because only the inner protrusions 109b and 112b can potentially interfere with each other (if these inner protrusions are both made straight, both curve in the same direction, etc.). In yet a different embodiment, only one extension member 106a or 106b includes two protrusions 109a and 109b or 112a and 112b, respectively, while the other extension member is coupled to its associated central member at only one pivot point, e.g. only the outer protrusion 109a or 112a is provided. This embodiment can be used, for example, if only one axis or degree of freedom of the device bears most of the force load of the device, so that the extra support of dual protrusions is only needed on one axis of the device. However, such an embodiment has a disadvantage in that the extension members are not symmetrical.

Joystick handle 16 (not shown) is coupled to one of the central members 108a or 108b (member 108a in FIG. 4) of gimbal mechanism 100 such that it extends out of the plane defined by axes D and E. An extension 119 can be coupled to or be part of central member 108a to which the joystick handle 16 is attached; alternatively, the extension 119 (or a longer similar member) of the central member 108a can itself be the user object 14, such as joystick handle 16. Gimbal mechanism 100 provides two rotary degrees of freedom to extension 119. The extension 119 can be rotated about axis A and B or have a combination of rotational movement about these axes. Extension 119 can be rotated about axis A by rotating extension member 106a, central member 108a, and central member 108b in a first revolute degree of freedom. Extension 119 can also be rotated about axis B by rotating extension member 106b and the two central members about axis B in a second revolute degree of freedom. As extension 119 (and joystick handle 16) is moved about axis A, floating axis D varies its position, and as extension 119 is moved about axis B, floating axis E varies its position.

In alternate embodiments, additional degrees of freedom can be provided. For example, the joystick handle 16/extension 119 can be rotated about axis C extending perpendicularly from the plane formed by floating axes D and E. This rotational degree of freedom can be provided with a sensor and/or an actuator to sense motion and apply forces in that degree of freedom. Additionally, a different degree of freedom can be added such that handle 16 can be linearly translated along floating axis C. This degree of freedom can also be sensed and actuated, if desired.

Extension members 106 of gimbal mechanism 100 are also coupled to belt drive mechanisms 114a and 114b. Mechanisms 114 are described in greater detail with respect to FIG. 7.

Figure 6:
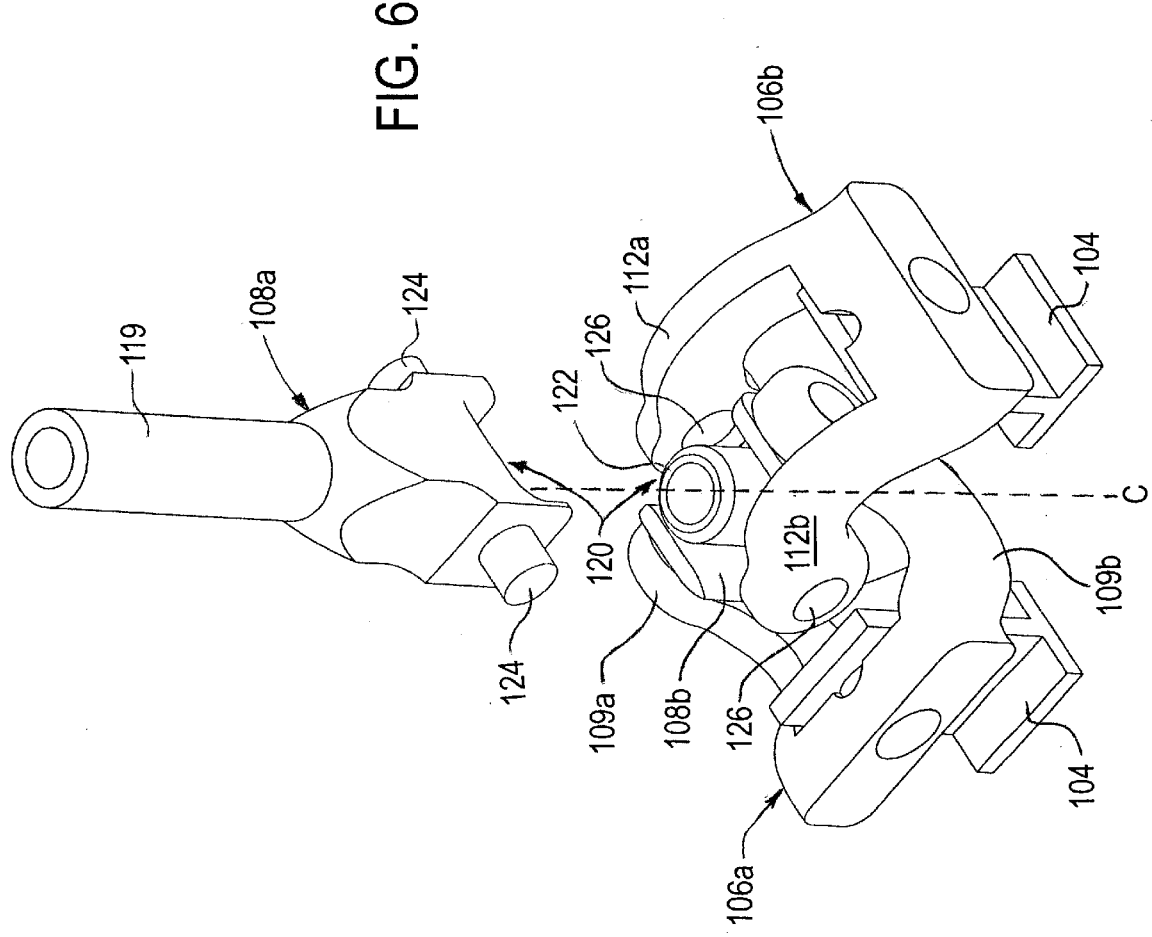
FIG. 6 is a partially exploded perspective view of the linkage mechanism of FIG. 6.

FIG. 6 is a partially exploded perspective view of gimbal mechanism 100. Central member 108a is shown decoupled from central member 108b to show the bearing 120 that connects the two members 108a and 108b. Bearing 120 includes a boss 122 that is coupled to extension member 108b as shown in FIG. 6, and which fits into a recess (not shown) in central member 108a. This bearing allows the two central members 108a and 108b to rotate with respect to each other about axis C. This rotation enables the range of motion in the two degrees of freedom about axes A and B as permitted by aperture 117 in plate 115, which in the described embodiment is about 15–25° of motion about either axis, but can be other ranges in other embodiments. Also, in other embodiments, the central members 108a and 108b can be shaped in alternate ways to allow greater or less rotation, depending on the desired range of motion in the two degrees of freedom.

Also shown in FIG. 6 is a preferred form of connection between the central members 108 and the extension members 106. Central member 108a includes bosses 124 which rotatably sit within apertures 126 of extension member 106b. In other embodiments, the bosses 124, for example, can be keyed, with slots provided in the protrusions 109 and 112 to allow the member 108 to slide into position between the protrusions without having to substantially flex the protrusions. Other types of bearings may be used in alternate embodiments.

Figure 7:
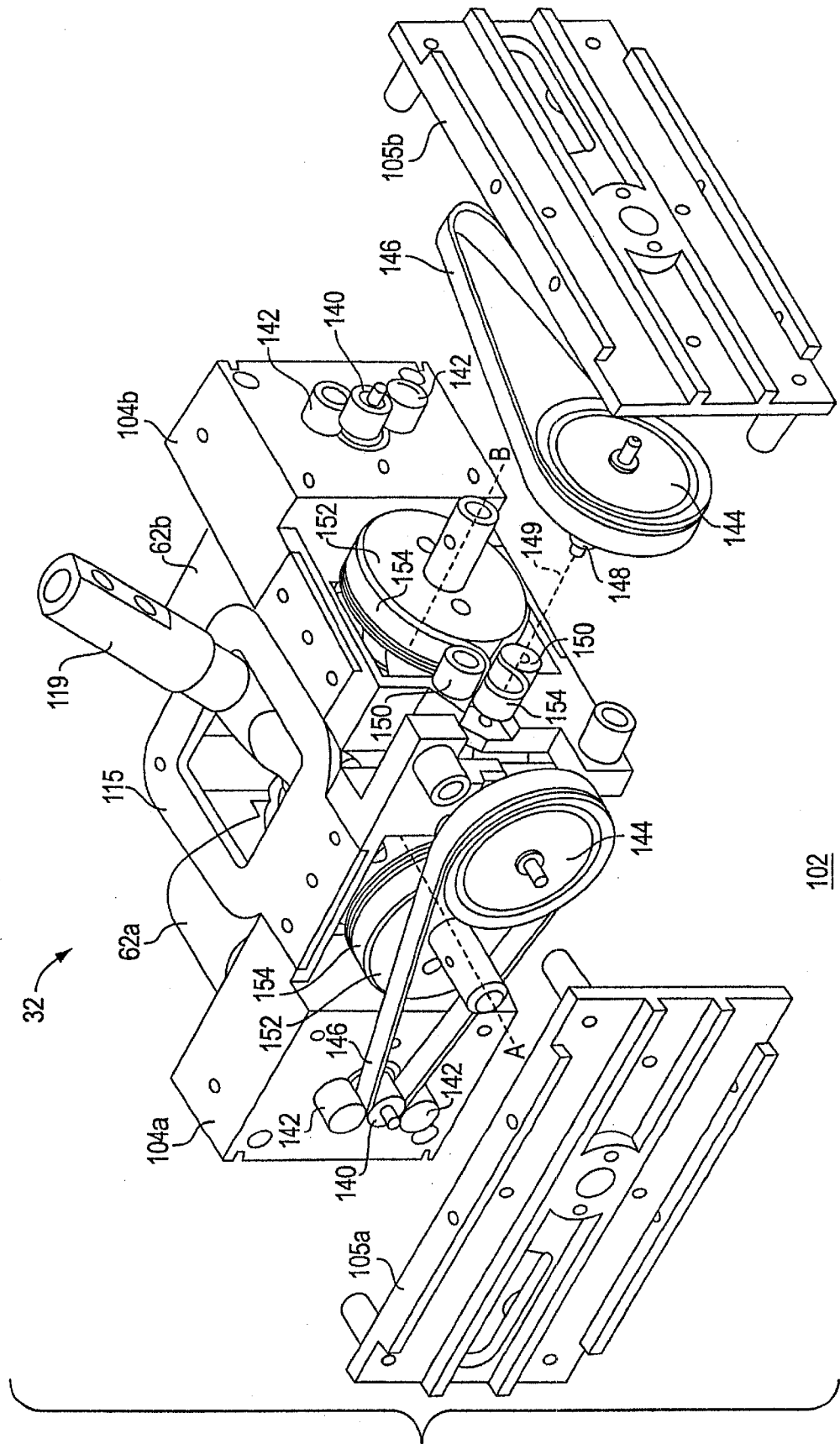
FIG. 7 is a perspective view of a the belt transmission system of the present invention.
Figure 8:
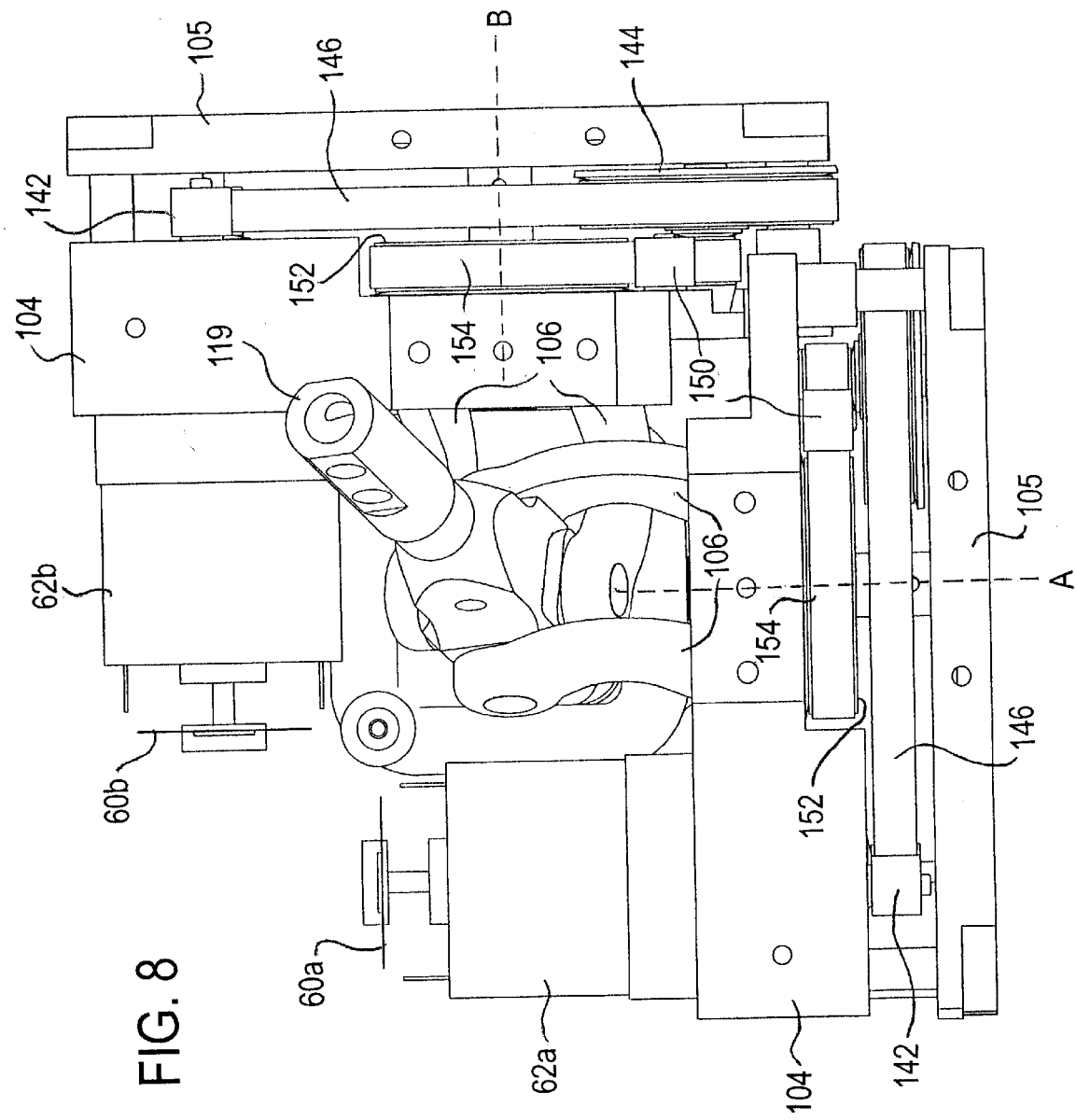
FIG. 8 is a top plan view of the force feedback device of FIG. 3.

FIG. 7 is a partially exploded perspective view of the mechanical apparatus 32 showing belt drive mechanisms 114a and 114b. FIG. 8 shows a top plan view of the mechanical apparatus 32. The belt drive mechanisms 114 are provided between the actuators 62 and the extension members 106 of the gimbal mechanism 100. Each belt drive mechanism 114 includes a first stage and a second stage, where the first stage includes drive pulley 140, passive idlers 142, first amplification pulley 144, and first belt 146, and where the second stage includes driven pulley 148, active idlers 150, second amplification pulley 152, and second belt 154.

The first stage includes drive pulley 140, which is coupled to the rotor of actuator 62. Drive pulley 140 may rotate freely when the actuator 62 is unpowered and may be driven in either rotational direction when the actuator is powered. First belt 146 is wrapped around drive pulley 140 and is also wrapped around first amplification pulley 144. First amplification pulley 144 is preferably about 4 to 4.5 times the diameter of drive pulley 140; other sizes may also be used in other embodiments. Belt 146 preferably includes teeth on the inner side of the belt or other gripping features that engage drive pulley 140 and amplification pulley 144, as described in greater detail with respect to FIG. 10. Passive idlers 142 of the present invention are positioned "adjacent" to drive pulley 140, preferably not contacting the drive pulley or belt 146 but being a close distance away. The passive idlers are provided to prevent the belt 146 from jumping off or moving radially away from drive pulley 140 when slack or compliance is present in first belt 146. The operation of passive idlers 142 is described in greater detail subsequently. Passive idlers 142 preferably have smooth outer surfaces and no teeth, since they are facing and can only contact a flat outer surface of belt 146. Two passive idlers 142 are preferably used as shown to effectively impede radial belt jumping in both directions of the associated degree of freedom of user object 14; in other embodiments, one passive idler or more than two passive idlers can be provided.

The second stage includes driven pulley 148, which is rigidly coupled to first amplification pulley 144 and is positioned such that second belt 154 is wrapped around pulley 148, as indicated by dashed line 149. The assembly of pulley 144/pulley 148 is rotatably coupled to ground member 104 and other ground member 105. Second amplification pulley 152 is rigidly coupled to extension member 106 of the gimbal mechanism 100. Second belt 152 is wrapped around transmission pulley 148 and second amplification pulley 152, and is routed around the active idlers 150 which are located at intermediate positions between pulleys 148 and 152 as shown. Active idlers 150 are positioned such that the belt 152 is routed between the driven pulley 148 and the active idlers 150, and the belt 152 is preferably routed around a portion of the circumference of each active idler. Active idlers 150 preferably have smooth cylindrical surfaces since they engage a flat outer surface of second belt 154. Unlike passive idlers 142, which are not in constant contact with first belt 146, the active idlers 150 are in constant rolling action with the second belt 154. This constant contact, and the position of the active idlers, increases the belt wrap angle of the belt around the pulley (i.e. to increase the number of belt teeth engaged with the pulley). This reduces the tendency of second belt 154 to slip and/or move or jump radially away from the driven pulley without adding tension to the belt. Two active idlers 150 are preferably provided as shown, where each active idler is most effective in one direction of motion of the associated degree of freedom of user object 14. In other embodiments, one active idler can be used, especially if only one direction to a degree of freedom is used, or more than two active idlers may also be used. Second amplification pulley 152 is preferably about 4 to 4.5 times the diameter of driven pulley 148, but other size ratios may be used in other embodiments. Belt 154 preferably includes teeth on an inner side or other gripping features that engage driven pulley 148 and amplification pulley 152, as described in greater detail with respect to FIG. 10.

The belt drive mechanisms 114 operate as follows. Actuator 62 outputs a rotational force on drive pulley 140, which rotates the pulley 140. This rotation causes first belt 146 to move and rotate pulley 144, which amplifies the force of rotation of pulley 140 based on the ratio between the radial sizes of pulley 144 and pulley 140. Pulley 148 rotates with pulley 144 and drives second belt 154, which in turn rotates pulley 152. Pulley 152 amplifies the force of rotation of pulley 148 based on the ratio between the diameters of pulley 148 and pulley 152.

The belt drive mechanism 114 provides a mechanical advantage to the output forces of actuators 62 so that the force output of the actuators is increased. The ratio of the diameter of pulley 144 to the diameter of pulley 140, and the ratio of the diameter of pulley 152 to pulley 148, dictates the amount of mechanical advantage, similar to a gear system. Since there are two stages, each providing amplification to the forces output by actuator 62, the total amplification to the forces is the product of the amplification provided by each stage. Thus, in the described embodiment, a total of 20:1 mechanical advantage is provided by both stages. Other ratios can be used in other embodiments depending on the desired amplification and space constraints. It should be noted that driven pulley 148 can also generically be considered a "drive pulley" since it drives the belt 154, and in other embodiments the driven pulley 148 can be directly coupled to an actuator 62.

Belt drive mechanisms 114 of the present invention are used in a force feedback interface device, in which friction is desired to be minimized to allow greater fidelity force sensations to be transmitted to the user. Since tensioned belt drives typically introduce a large amount of friction, the belt drive mechanisms described herein engage the belts with the pulleys using a positive gripping feature, such as interlocking teeth (or the equivalent), rather than tensioning the belts tightly around pulleys. With little tension in the system, little friction is introduced. In addition, since belts are used rather than directly interlocking gears, backlash problems are minimized. Higher quality force sensations thus can be provided with all the advantages of an amplification transmission system.

However, since there is little tension in the belt system, the belt can have the tendency to ride up or move radially away from the pulley around which it is routed since temporary slack in the belt can be introduced. To minimize this problem, passive idlers 142 and active idlers 150 of the present invention are used. Passive idlers 142 are used to prevent any slack in the first belt 146 from causing the belt 146 to jump up and away from the pulley 140 or cause other disturbances in the transmission of forces from actuator 62 to gimbal mechanism 100. For example, actuator 62 may suddenly rotate in an opposite direction, which can cause the belt 146 tension to change significantly. This change is tension often causes the belt to try to move away from pulley 140 or ride up toward either of idlers 142. Idlers 142 are therefore positioned to stop any such movement of the belt and to keep the belt smoothly moving about pulley 140 after such a disturbance. The passive idlers 142 are preferably rotatably coupled to grounded member 104 and thus only a small amount of rotary friction is introduced when the belt contacts the passive idler, allowing the belt to continue moving and transmitting motion and forces after impacting the idlers during such sudden motions or other disturbances in the operation of the belt drive. Alternatively, passive idlers 142 can be rigidly coupled to grounded member 104, which may cause more friction when the idlers contact the belt.

Active idlers 150 are also provided to prevent unwanted movement of a belt with respect to a drive pulley such as driven pulley 148. The active idlers 150 are positioned to cause a greater portion of belt 154 to engage with driven pulley 148, e.g. a greater number of teeth of the belt 154 are engaged with teeth of pulley 148 than if no active idlers were used. This is also known as increasing the "wrap angle" of the belt on the pulley, or increasing the "teeth in mesh" between pulley and belt. This provides driven pulley 148 with a greater grip on belt 154, which is needed since driven pulley 148 rotates with amplified torques. Without the active idlers 150, the belt 154 can slip with respect to the pulley 148 and also ride up or move radially away from pulley 148. However, it is also important to note that active idlers 150 do not add significant tension to the belt drive mechanisms 114. The active idlers are positioned to guide or influence the path of the belt 154 around pulley 148 but not to significantly stretch the belt, preload the belt, or otherwise cause tension in the belt, which could occur if the active idlers were positioned closer to each other between the driven pulley 148 and the second amplification pulley 152. Thus, the active idlers 150 are preferably positioned as close as possible to each other to increase the wrap angle of the belt without introducing preload in the belt 154, i.e. with just enough distance between them so that no preload is introduced in the belt. This allows the force sensations to not be corrupted by friction caused by tension in the belt.

In other embodiments, passive idlers and/or active idlers can be positioned at other locations in the belt drive mechanism, such as at different pulleys than in the described embodiment. In addition, only one stage can be provided in the belt drive mechanism. In such an embodiment, active idlers are preferably used adjacent to the drive pulley instead of the passive idlers to achieve more effective belt engagement. In other embodiments, more than two stages can be provided; preferably, the stages further from the actuator that receive greater amplification use active idlers similar to idlers 150.

Figure 9A:
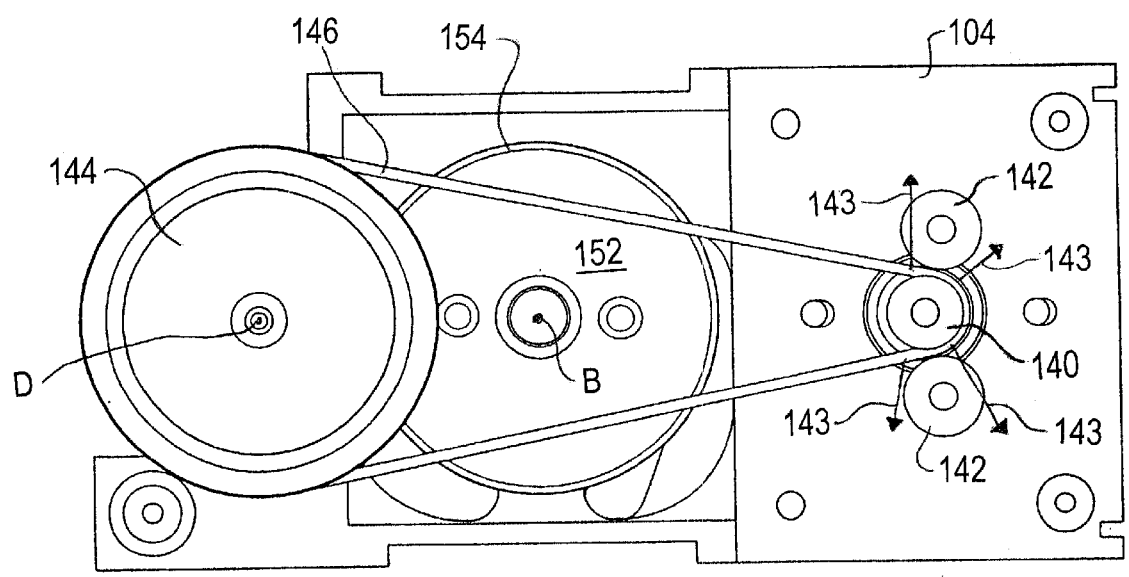
FIGS. 9a and 9b are side plan views of the belt transmission system of FIG. 7.
Figure 9B:
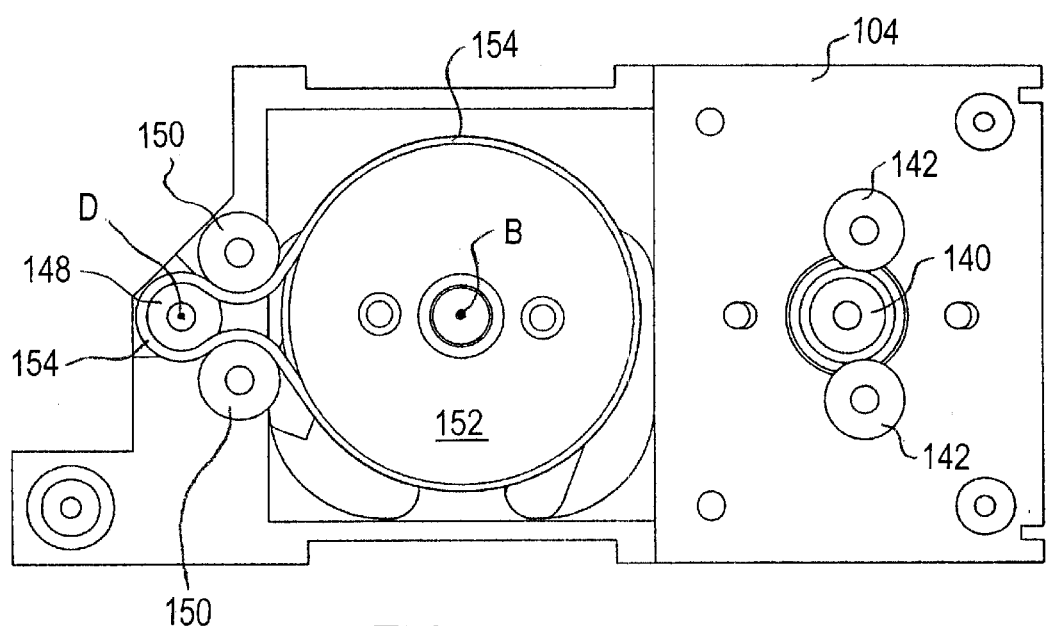

FIGS. 9a and 9b are side elevation views of the belt drive mechanism 114 of the present invention. FIG. 9a shows the first stage of the belt drive, in which drive pulley 140 is connected to amplification pulley 144 by first belt 146. The passive idlers 142 are shown positioned just adjacent to the belt 146 on either side of drive pulley 140 with sufficient offset to insure a non-contact relationship during typical operation. The idlers 142, however, are in close enough proximity to prevent any significant radial movement of the belt 146 away from drive pulley 140 due to slack or compliance in the belt during rotation of the belt and pulleys. Such radial movement that is reduced or prevented by the passive idlers is shown by arrows 143. FIG. 9b shows the second stage of the belt drive after the first stage amplification pulley 144 and belt 146 have been removed, where the driven pulley 148 is coupled to the second amplification pulley 152 by a belt 154, and where active rollers 150 contact the belt 154 without adding tension or preload to the belt. First amplification pulley 144 and transmission pulley 148 are rigidly coupled together and both rotate about axis D.

Figure 10:
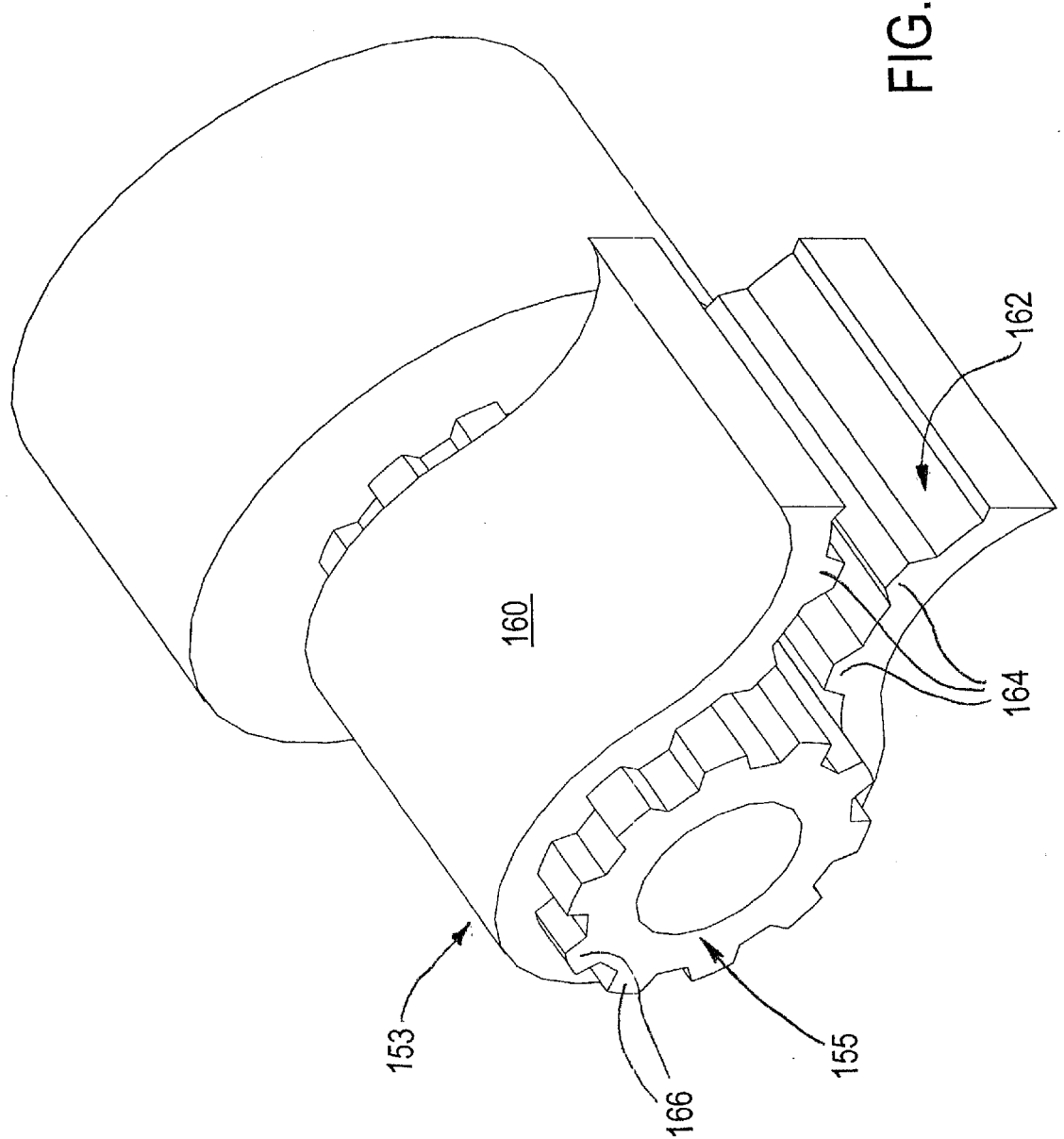
FIG. 10 is a perspective view of an example of a synchronous belt and drive pulley engaged with the belt for use in the present invention.

FIG. 10 is a perspective view of an example of a belt 153, which can be belt 146 or 154, engaged with a pulley 155, which can be any of pulleys 140, 144, 148, or 152, for example. It should be noted that since the belt in the example of FIG. 10 has a wrap angle greater than 180 degrees around the pulley, FIG. 10 most accurately represents driven pulley 148 and belt 154 of the described embodiment without showing active idlers 150. The actual relative size of the pulley and belt and number of teeth used on belt and pulley can vary depending on the particular pulley, belt, and/or embodiment. Belt 153 is a flexible member formed in a loop, with a flat surface on an outer side 160. Belt 153 is preferably a positive grip belt, i.e. a belt having gripping features, such as teeth on an inner side of the belt, that engage the pulley 155, e.g. the teeth of the belt mate with other gripping features (e.g. teeth) of the pulley 155 (a "synchronous belt"). Belt 153 thus preferably includes evenly-spaced teeth 164 on an inner side 162 that engage teeth 166 of the pulley as shown. Belt 153 is preferably made of a material having high strength and abrasion resistance, such as urethane reinforced with polyester cords. As used herein, a "belt drive" or "belt drive transmission" refers to a transmission including such flat, toothed types of belts or V-belts, as distinguished from cables or other flexible members.

While this invention has been described in terms of several preferred embodiments, it is contemplated that alterations, modifications and permutations thereof will become apparent to those skilled in the art upon a reading of the specification and study of the drawings. For example, the user manipulatable object, sensors and actuators used can be a variety of types. Furthermore, certain terminology has been used for the purposes of descriptive clarity, and not to limit the present invention. It is therefore intended that the following appended claims include all such alterations, modifications and permutations as fall within the true spirit and scope of the present invention.

What is claimed is:

1. A force feedback device capable of communicating with a host computer, the force feedback device comprising:
   a user manipulatable object graspable by a user;
   a linkage mechanism coupled to said user manipulatable object and providing said user manipulatable object with first and second rotary degrees of freedom, said linkage mechanism including:
      a grounded member coupled to a ground;
      a first extension member and a second extension member rotatably coupled to said grounded member; and
      a first central member rotatably coupled to said first extension member and a second central member rotatably coupled to said second extension member, wherein said first and second central members are rotatably coupled to each other, and wherein said first extension member and said first central member are substantially identical to and positioned symmetrically to said second extension member and said second central member;
   first and second actuators coupled to said linkage mechanism, said first actuator operative to output a force in said first degree of freedom and said second actuator operative to output a force in said second degree of freedom;
   at least one sensor operative to sense motion of said user manipulatable object in said first and second degrees of freedom; and
   a belt drive transmission coupled between said first actuator and said linkage mechanism, said belt drive transmission including a synchronous belt.

2. A force feedback device as recited in claim 1 wherein said first and second extension members each include two protrusions, each of said protrusions rotatably coupled to said first and second central members, respectively.

3. A force feedback device as recited in claim 2 wherein portions of said first and second extension members extend out of a plane formed by axes of rotation for said first and second degrees of freedom.

4. A force feedback device as recited in claim 3 wherein said portions that extend out of said plane are a middle portion of at least one of said protrusions of each of said extension members.

5. A force feedback device as recited in claim 4 wherein one of said protrusions of said first extension member extend out of said plane on a first side of said plane, and wherein one of said protrusions of said second extension member extend out of said plane on a second side of said plane opposite to said first side.

6. A force feedback device as recited in claim 5 wherein both of said protrusions of said first extension member extend out of said plane on said first side, and wherein both of said protrusions of said second extension member extend out of said plane on said second side.

7. A force feedback device as recited in claim 4 wherein said protrusions of said first extension member are rotatably coupled to first central member such that said first central member is positioned between said protrusions of said first extension member, and wherein said protrusions of said second extension member are rotatably coupled to second central member such that said second central member is positioned between said protrusions of said second extension member.

8. A force feedback device as recited in claim 1 wherein said belt drive transmission is a first belt drive transmission coupled to said first actuator, and further comprising a second belt drive transmission coupled between second actuator and said linkage mechanism.

9. A force feedback device as recited in claim 8 wherein said first belt drive transmission is symmetrical to said second belt drive transmission.

10. A force feedback device as recited in claim 9 wherein said at least one sensor includes a first sensor coupled to said first actuator and a second sensor coupled to said second actuator.

11. A force feedback device capable of communicating with a host computer, the force feedback device comprising:
   a user manipulatable object graspable by a user;
   a linkage mechanism coupled to said user manipulatable object and providing said user manipulatable object with first and second rotary degrees of freedom, said linkage mechanism including:
      a ground member;
      a first extension member coupled to said ground member and rotatable about a first fixed axis of rotation, and a second extension member rotatably coupled to said ground member and rotatable about a second fixed axis of rotation, wherein said first and second extension members each include two protrusions; and
      a first central member rotatably coupled to said two protrusions of said first extension member between said two protrusions of said first extension member such that said first central member is supported on two of its sides by said first extension member, and a second central member rotatably coupled to said two protrusions of said second extension member between said two protrusions of said second extension member such that said second central member is supported on two of its sides by said second extension member, and wherein said first and second central members are rotatably coupled to each other and are rotatable about first and second floating axes, respectively, wherein when said user manipulatable object is positioned in a origin position, couplings between said first central member and said protrusions of said first extension member intersect said second fixed axis of rotation, and couplings between said second central member and said protrusion of said second extension member intersect said first fixed axis of rotation, wherein said floating axes are movable with respect to said ground, and said floating axes are coincident with said fixed axes of rotation when said user manipulatable object is positioned in said origin position;
   first and second actuators coupled to said linkage mechanism, said first actuator operative to output a force in said first degree of freedom and said second actuator operative to output a force in said second degree of freedom; and
   at least one sensor operative to sense motion of said user manipulatable object in said first and second degrees of freedom.

12. A force feedback device as recited in claim 11 wherein portions of said first and second extension members extend out of a plane formed by said floating axes of rotation for said first and second degrees of freedom.

13. A force feedback device as recited in claim 12 wherein said portions that extend out of said plane are a middle portion of at least one of said protrusions of each of said extension members.

14. A force feedback device as recited in claim 13 wherein at least one of said protrusions of said first extension member extend out of said plane on a first side of said plane, and wherein at least one of said protrusions of said second extension member extend out of said plane on a second side of said plane opposite to said first side.

15. A force feedback device as recited in claim 11 wherein said first extension member and said first central member are substantially identical to and positioned symmetrically to said second extension member and said second central member.

16. A force feedback device as recited in claim 11 further comprising a belt drive transmission coupled between said first actuator and said linkage mechanism, said belt drive transmission including a synchronous belt.

17. A force feedback device as recited in claim 11 wherein said protrusions of said first extension member extend in planes parallel to said fixed axis of rotation, and wherein said two protrusions of said second extension member extend on planes parallel to said second fixed axis of rotation.

18. A force feedback interface device capable of communicating with a host computer and providing forces to a user manipulating said interface device, the interface device comprising:
   a user manipulandum for physical contact by a user and moveable in two degrees of freedom;
   a sensor for detecting a position of said user manipulandum in said degrees of freedom; and
   a linkage mechanism coupled between said user manipulandum and a physical ground, said linkage mechanism providing said two degrees of freedom to said user manipulandum, wherein said linkage mechanism includes a serially-linked chain of rotatable members coupled to ground at both ends of said chain, said chain including:
      a first member including two protrusions;
      a second member rotatably coupled to said first member between said two protrusions of said first member;
      a third member rotatably coupled to said second member, and
      a fourth member including two protrusions and rotatably coupled to said third member, wherein said third member is coupled between said protrusions of said fourth member,
   wherein when said user manipulatable object is in an origin position, a first coupling between said first member and said physical ground and a third coupling between said third member and said fourth member are aligned on one of said fixed axes of rotation, and a second coupling between said first member and said second member and a fourth coupling between said fourth member and said ground are aligned on a different one of said fixed axes of rotation, said first member and said fourth member being rotatable about said two fixed axes of rotation, and wherein said second member and said third member are rotatable about first and second floating axes, said floating axes being movable with respect to said ground.

19. A force feedback interface device as recited in claim 18 wherein middle portions of at least one of said protrusions of said first and fourth members extend out of a plane formed by axes of rotation for said two degrees of freedom.

20. A force feedback interface device as recited in claim 19 wherein said protrusions of said first and fourth members include an inner protrusion and an outer protrusion, wherein said inner protrusion of said first member extends out of said plane on a first side of said plane, and wherein said inner protrusion of said fourth member extends out of said plane on a second side of said plane opposite to said first side.

21. A force feedback interface device as recited in claim 18 further comprising an actuator coupled to said user manipulandum for applying a force to said user manipulandum, wherein at least part of said linkage mechanism is coupled between said actuator and said user manipulandum.

22. A force feedback interface device as recited in claim 21 further comprising a belt drive transmission coupled between said actuator and said user manipulatable object, said belt drive transmission including a drive pulley coupled to said actuator, a belt coupling said drive pulley to an amplification pulley, and an idler positioned adjacent to said drive pulley, said idler being positioned to impede radial displacement of a belt away from said drive pulley and thus loss of positive engagement during normal operation without preloading said belt.

23. A force feedback device as recited in claim 22 wherein said idler is an a passive idler positioned adjacent to said drive pulley, said passive idler not contacting said belt wrapped around said drive pulley normal operation and preventing said belt from moving off said drive pulley when slack is introduced in said belt.

24. A force feedback device as recited in claim 22 wherein said idler is an active idler positioned adjacent to said drive pulley and is continually contacting said second belt during normal operation of said belt drive transmission, wherein said active idler increases a wrap angle of said belt on said drive pulley.

25. A force feedback interface device as recited in claim 23 wherein said drive pulley, said amplification pulley and said passive idlers are included in a first stage of said belt drive transmission, and wherein said belt drive transmission further comprises a second stage including a second belt.

26. A force feedback interface device as recited in claim 25 wherein said second stage includes a driven pulley rigidly coupled to said amplification pulley, and a second amplification pulley coupled to said driven pulley by said second belt.

27. A force feedback device as recited in claim 21 wherein said belt drive transmission is a first belt drive transmission coupled to said first actuator, and further comprising a second belt drive transmission coupled between said second actuator and said linkage mechanism.

28. A force feedback device as recited in claim 27, wherein said at least one sensor includes a first sensor coupled to said first actuator and a second sensor coupled to said second actuator.

29. A force feedback device capable of communicating with a host computer, the interface device comprising:
  a user manipulatable object physically contactable by a user;
  a linkage mechanism coupled to said user manipulatable object and providing said user manipulatable object with first and second rotary degrees of freedom, said linkage mechanism including:
    a ground member;
    a first extension member and a second extension member rotatably coupled to said ground member; and
    a first central member rotatably coupled to said first extension member, and a second central member rotatably coupled to said second extension member, and wherein said first and second central members are rotatably coupled to each other;
  first and second actuators coupled to said linkage mechanism, said first actuator operative to output a force in said first degree of freedom and said second actuator operative to output a force in said second degree of freedom;
  at least one sensor operative to sense motion of said user manipulatable object in said first and second degrees of freedom; and
  a belt drive transmission coupled between said first actuator and said linkage mechanism, said belt drive transmission including a synchronous belt.

30. A force feedback device as recited in claim 29 wherein said first belt drive transmission is symmetrical to said second belt drive transmission.

31. A force feedback interface device capable of communicating with a host computer and providing forces to a user manipulating said interface device, the interface device comprising:
  a user manipulandum for physical contact by a user and moveable in two degrees of freedom;
  a sensor for detecting a position of said user manipulandum in said degrees of freedom;
  an actuator coupled to said user manipulandum for applying a force to said user manipulandum;
  a belt drive transmission coupled between said actuator and said user manipulatable object, said belt drive transmission including a drive pulley coupled to said actuator, a belt coupling said drive pulley to an amplification pulley, and an idler positioned adjacent to said drive pulley, said idler being positioned to impede radial displacement of a belt away from said drive pulley and thus loss of positive engagement during normal operation without preloading said belt; and
  a linkage mechanism coupled between said actuator and said user manipulandum and coupled to a physical ground, said linkage mechanism providing said two degrees of freedom to said user manipulandum and transmitting said force from said actuator to said user manipulandum, wherein said linkage mechanism includes a serially-linked chain of rotatable members coupled to ground at both ends of said chain, said chain including:
    a first member;
    a second member rotatably coupled to said first member;
    a third member rotatably coupled to said second member, and a fourth member rotatably coupled to said third member.

32. A force feedback device as recited in claims 31 wherein said idler is a passive idler positioned adjacent to said drive pulley, said passive idler not contacting said belt wrapped around said drive pulley during normal operation and preventing said belt from moving off said drive pulley when slack is introduced in said belt.

33. A force feedback interface device as recited in claim 32 wherein said drive pulley, said amplification pulley and said passive idlers are included in a first stage of said belt drive transmission, and wherein said belt drive transmission further comprises a second stage including a second belt.

34. A force feedback interface device as recited in claim 33 wherein said second stage includes a driven pulley rigidly coupled to said amplification pulley, and a second amplification pulley coupled to said driven pulley by said second belt.

35. A force feedback device as recited in claim 31 wherein said idler is an active idler positioned adjacent to said drive pulley and is continually contacting said second belt during normal operation of said belt drive transmission, wherein said active idler increases a wrap angle of said belt on said drive pulley.

\* \* \* \* \*